United States Patent
O'Brien, III et al.

(10) Patent No.: US 12,048,823 B2
(45) Date of Patent: Jul. 30, 2024

(54) NEEDLING DEVICE FOR USE WITH DISPOSABLE NEEDLE CARTRIDGES

(71) Applicant: Crown Laboratories, Inc., Johnson City, TN (US)

(72) Inventors: Thomas Michael O'Brien, III, Dallas, TX (US); John Tepper, Carrollton, TX (US); Jeffrey Garrett, Allen, TX (US)

(73) Assignee: CROWN LABORATORIES, INC., Johnson City, TN (US)

( * ) Notice: Subject to any disclaimer, the term of this patent is extended or adjusted under 35 U.S.C. 154(b) by 1270 days.

(21) Appl. No.: 16/264,974

(22) Filed: Feb. 1, 2019

(65) Prior Publication Data

US 2019/0160274 A1    May 30, 2019

Related U.S. Application Data

(63) Continuation of application No. 15/495,564, filed on Apr. 24, 2017, now Pat. No. 10,220,195, which is a
(Continued)

(51) Int. Cl.
*A61M 37/00* (2006.01)
*A61B 18/00* (2006.01)
(Continued)

(52) U.S. Cl.
CPC ..... *A61M 37/0015* (2013.01); *A61B 18/1477* (2013.01); *A61M 5/2033* (2013.01);
(Continued)

(58) Field of Classification Search
CPC .. A61M 37/0015; A61M 5/2033; A61M 5/46; A61M 37/0084; A61M 5/3298;
(Continued)

(56) References Cited

U.S. PATENT DOCUMENTS 2,578,812 A    12/1951 Kollsman
2,588,623 A    3/1952 Eliscu et al.
(Continued)

FOREIGN PATENT DOCUMENTS

CA    2340248 A1    2/2000
CA    2696209 A1    2/2009
(Continued)

OTHER PUBLICATIONS

SkinPen Precision webpages, Bellus Medical, http://insidesales.skinpen.com, www.skinpen.com, 5 pgs.
(Continued)

*Primary Examiner* — James D Ponton
(74) *Attorney, Agent, or Firm* — KDW FIRM PLLC

(57) ABSTRACT

Disclosed herein are transdermal microneedling devices that generate and emit low RF energy. Such a microneedling device may comprise a drive motor, drive circuitry for controlling the drive motor, and a drive linkage located on the drive motor rotor. The microneedling device may also comprise a power source capsule comprising a battery and associated power management circuitry. Also included may be a needle cartridge coupled to the main body, and comprising a drive shaft and a needle unit coupled to a distal end of the drive shaft to move therewith, where the needle unit has at least one needle extending therefrom. The drive shaft may comprise a linkage member configured to engage the drive linkage of the drive motor, and be configured to be driven by the drive motor and thereby drive movement of the needle unit such that the at least one needle extends beyond and retracts within the distal end of the needle cartridge. The microneedling device may also include RF energy circuitry powered by the power source and configured to generate RF energy, as well as transfer circuitry configured to transfer the
(Continued)

generated RF energy from the RF energy circuitry to the at least one needle.

16 Claims, 14 Drawing Sheets

Related U.S. Application Data continuation-in-part of application No. 15/356,079, filed on Nov. 18, 2016, now Pat. No. 9,629,991, which is a continuation-in-part of application No. 15/176,223, filed on Jun. 8, 2016, now Pat. No. 9,636,491.

(51) Int. Cl.

| | | |
|---|---|---|
| *A61B 18/14* | (2006.01) | |
| *A61B 90/00* | (2016.01) | |
| *A61M 5/20* | (2006.01) | |
| *A61M 5/315* | (2006.01) | |
| *A61M 5/32* | (2006.01) | |
| *A61M 5/46* | (2006.01) | |
| *A61N 1/40* | (2006.01) | |

(52) U.S. Cl.
CPC .......... *A61M 5/46* (2013.01); *A61M 37/0084* (2013.01); *A61N 1/40* (2013.01); *A61B 2018/00196* (2013.01); *A61B 2018/00452* (2013.01); *A61B 2018/1425* (2013.01); *A61B 2018/143* (2013.01); *A61B 2018/1475* (2013.01); *A61B 2090/036* (2016.02); *A61B 2218/002* (2013.01); *A61M 2005/31588* (2013.01); *A61M 5/3298* (2013.01); *A61M 2037/0023* (2013.01); *A61M 2205/054* (2013.01); *A61M 2205/368* (2013.01); *A61M 2205/8206* (2013.01)

(58) Field of Classification Search
CPC .......... A61M 2005/31588; A61M 2037/0023; A61M 2205/054; A61M 2205/368; A61M 2205/8206; A61M 2037/0007; A61M 2205/11; A61M 2205/273; A61M 2205/8243; A61B 18/1477; A61B 2018/00196; A61B 2018/00452; A61B 2018/1425; A61B 2018/143; A61B 2018/1475; A61B 2090/036; A61B 2218/002; A61N 1/40; A61N 1/36017
See application file for complete search history.

(56) References Cited

U.S. PATENT DOCUMENTS

| | | | |
|---|---|---|---|
| 2,840,076 | A | 6/1958 | Robbins |
| 3,750,667 | A | 8/1973 | Pshenichney et al. |
| 4,159,659 | A | 7/1979 | Nightingale |
| 4,204,438 | A | 5/1980 | Binaris et al. |
| 4,372,315 | A * | 2/1983 | Shapiro .......... A61B 18/14 606/36 |
| 4,582,060 | A | 4/1986 | Bailey |
| 4,671,277 | A | 6/1987 | Beuchat |
| 4,782,725 | A | 11/1988 | Spaulding |
| 4,796,624 | A | 1/1989 | Trott et al. |
| 4,798,582 | A | 1/1989 | Sarath et al. |
| 5,279,552 | A * | 1/1994 | Magnet .......... A61M 37/0076 604/47 |
| 5,514,150 | A | 5/1996 | Rostoker |
| 5,551,319 | A | 9/1996 | Spaulding et al. |
| 5,676,684 | A | 10/1997 | Choi |
| 5,697,901 | A | 12/1997 | Eriksson |
| 5,735,868 | A | 4/1998 | Lee |
| 5,741,290 | A | 4/1998 | Hsieh |
| 5,935,096 | A | 8/1999 | Barrett |
| 5,976,167 | A | 11/1999 | Lee |
| 6,080,172 | A | 6/2000 | Fujiwara et al. |
| 6,332,871 | B1 | 12/2001 | Douglas et al. |
| 6,345,553 | B1 | 2/2002 | Adler et al. |
| 6,503,231 | B1 | 1/2003 | Prausnitz et al. |
| 6,505,530 | B2 | 1/2003 | Adler et al. |
| 6,537,242 | B1 * | 3/2003 | Palmer .......... A61M 37/0015 600/583 |
| 6,793,633 | B2 | 9/2004 | Douglas et al. |
| 6,890,319 | B1 | 5/2005 | Crocker |
| 7,207,242 | B1 | 4/2007 | Daigle |
| 7,340,980 | B2 | 3/2008 | Conti Vecchi |
| 7,422,574 | B2 | 9/2008 | Eriksson et al. |
| 7,470,237 | B2 | 12/2008 | Beckman et al. |
| 7,618,429 | B2 | 11/2009 | Mulholland |
| 7,695,486 | B2 | 4/2010 | Dixon |
| 7,908,943 | B2 | 3/2011 | Beyer |
| 8,029,527 | B2 | 10/2011 | Lisec |
| 8,202,249 | B2 | 6/2012 | Iio et al. |
| 8,236,021 | B2 | 8/2012 | Kluge et al. |
| 8,454,643 | B2 | 6/2013 | Crockett |
| 8,540,705 | B2 | 9/2013 | Mehta |
| 8,556,828 | B2 | 10/2013 | Amano et al. |
| 8,641,703 | B2 | 2/2014 | Flyash et al. |
| 8,666,487 | B2 | 3/2014 | Kang |
| 8,700,176 | B2 | 4/2014 | Azar et al. |
| 8,794,109 | B2 | 8/2014 | Lee |
| 8,900,194 | B2 | 12/2014 | Clarke et al. |
| 8,920,379 | B2 | 12/2014 | Lee |
| 8,945,056 | B2 | 2/2015 | Iio et al. |
| 9,005,158 | B2 | 4/2015 | Danenberg et al. |
| 9,044,582 | B2 | 6/2015 | Chang et al. |
| 9,364,392 | B2 | 6/2016 | Ko |
| 2003/0195542 | A1 | 10/2003 | Lee |
| 2005/0010236 | A1 | 1/2005 | Frister |
| 2005/0137525 | A1 | 6/2005 | Wang et al. |
| 2005/0222565 | A1 | 10/2005 | Manstein |
| 2005/0283125 | A1 | 12/2005 | Barkhahn et al. |
| 2006/0047254 | A1 | 3/2006 | Akahoshi |
| 2007/0038181 | A1 | 2/2007 | Melamud et al. |
| 2008/0009802 | A1 | 1/2008 | Lambino et al. |
| 2008/0009811 | A1 | 1/2008 | Cantor |
| 2008/0027384 | A1 | 1/2008 | Wang et al. |
| 2008/0119781 | A1 | 5/2008 | King |
| 2008/0214987 | A1 | 9/2008 | Xu |
| 2008/0306502 | A1 | 12/2008 | Lisec et al. |
| 2009/0125050 | A1 | 5/2009 | Dixon |
| 2009/0137945 | A1 | 5/2009 | Marquez |
| 2009/0209992 | A1 | 8/2009 | McConchie |
| 2009/0222000 | A1 | 9/2009 | Pacey |
| 2009/0318833 | A1 | 12/2009 | Lim |
| 2009/0326571 | A1 | 12/2009 | Mulholland |
| 2010/0023003 | A1 | 1/2010 | Mulholland |
| 2010/0030152 | A1 | 2/2010 | Lee et al. |
| 2010/0049126 | A1 | 2/2010 | Bronfeld et al. |
| 2010/0286618 | A1 | 11/2010 | Choi |
| 2011/0125179 | A1 | 5/2011 | Dell'Aquila et al. |
| 2011/0218464 | A1 | 9/2011 | Iger |
| 2011/0230839 | A1 | 9/2011 | Bahrami et al. |
| 2012/0041374 | A1 | 2/2012 | Lee |
| 2012/0123462 | A1 | 5/2012 | Lee |
| 2012/0158032 | A1 | 6/2012 | Jarling |
| 2012/0158100 | A1 | 6/2012 | Schomacker |
| 2012/0271335 | A1 | 10/2012 | Lee |
| 2012/0296280 | A1 | 11/2012 | Eum |
| 2014/0005658 | A1 | 1/2014 | Rosenbegr |
| 2014/0018835 | A1 | 1/2014 | Scherkowski et al. |
| 2014/0025062 | A1 | 1/2014 | Rosenberg et al. |
| 2014/0066864 | A1 | 3/2014 | Eum |
| 2014/0094742 | A1 | 4/2014 | Won |
| 2014/0094837 | A1 | 4/2014 | Danenberg |
| 2014/0155963 | A1 | 6/2014 | Ko |
| 2014/0343481 | A1 | 11/2014 | Ignon |
| 2014/0358200 | A1 | 12/2014 | Ko |
| 2015/0025561 | A1 | 1/2015 | La Fontaine |
| 2015/0057604 | A1 | 2/2015 | Arami et al. |
| 2015/0133862 | A1 | 5/2015 | Bang |

(56) References Cited

U.S. PATENT DOCUMENTS

| | | |
|---|---|---|
| 2015/0151098 A1 | 6/2015 | Spendlove et al. |
| 2015/0201825 A1 | 7/2015 | Na |
| 2015/0272648 A1* | 10/2015 | Leonard ............ A61B 17/8891 606/104 |
| 2015/0351798 A1 | 12/2015 | Bourland et al. |
| 2015/0352346 A1 | 12/2015 | Webb |
| 2015/0359559 A1* | 12/2015 | Scherkowski ... A61B 17/32093 606/186 |
| 2016/0074646 A1 | 3/2016 | Norman |
| 2016/0121093 A1 | 5/2016 | Fan |
| 2016/0175573 A1 | 6/2016 | Groop et al. |
| 2016/0271410 A1 | 9/2016 | Ko |

FOREIGN PATENT DOCUMENTS

| | | |
|---|---|---|
| CA | 2568482 C | 2/2011 |
| CA | 2688510 A1 | 4/2011 |
| CN | 1256930 C | 5/2006 |
| CN | 10053569 C | 10/2009 |
| CN | 101557848 A | 10/2009 |
| CN | 102271608 A | 12/2011 |
| CN | 202173684 U | 3/2012 |
| CN | 101605536 B | 5/2012 |
| CN | 202740626 U | 2/2013 |
| CN | 202961504 U | 6/2013 |
| CN | 204017141 U | 12/2014 |
| CN | 204411493 U | 6/2015 |
| CN | 103272326 B | 8/2015 |
| CN | 103282077 B | 8/2015 |
| DE | 4331442 A1 | 3/1995 |
| DE | 19836376 A1 | 2/2000 |
| DE | 202004010659 U1 | 10/2004 |
| DE | 19781097 B4 | 7/2006 |
| DE | 102008031907 A1 | 1/2010 |
| EP | 0955359 B1 | 11/1999 |
| EP | 1104315 B1 | 11/2004 |
| EP | 1495782 B1 | 1/2005 |
| EP | 1576982 B1 | 9/2005 |
| EP | 1679039 B1 | 7/2006 |
| EP | 1882491 B1 | 1/2008 |
| EP | 1958659 B1 | 8/2008 |
| EP | 1992387 A2 | 11/2008 |
| EP | 2178585 A2 | 4/2010 |
| EP | 2324877 A1 | 5/2011 |
| EP | 2450080 A2 | 5/2012 |
| EP | 2462979 B1 | 6/2012 |
| EP | 2633882 A1 | 9/2013 |
| EP | 2653061 B1 | 10/2013 |
| EP | 2420265 B1 | 11/2014 |
| EP | 2835147 A1 | 2/2015 |
| EP | 2944349 A1 | 11/2015 |
| EP | 2954925 A1 | 12/2015 |
| EP | 2954926 A1 | 12/2015 |
| GB | 1444355 | 7/1976 |
| GB | 2234420 A | 2/1991 |
| GB | 2514444 A | 11/2014 |
| GB | 2518021 A | 3/2015 |
| JP | 10127732 A2 | 5/1998 |
| JP | 2000177289 A | 6/2000 |
| JP | 3097600 B2 | 10/2000 |
| JP | 2001293095 A | 10/2001 |
| JP | 2010514479 T2 | 5/2010 |
| JP | 2011167476 A | 9/2011 |
| JP | 4983180 B2 | 7/2012 |
| JP | 5539396 B2 | 7/2014 |
| KR | 20100007720 U | 7/2010 |
| KR | 101395099 A | 1/2014 |
| KR | 101457437 A | 7/2014 |
| KR | 101494219 B1 | 2/2015 |
| WO | 8701337 | 3/1987 |
| WO | 9742888 | 11/1997 |
| WO | 0009184 | 2/2000 |
| WO | 2004009172 A1 | 1/2004 |
| WO | 2004075971 A1 | 9/2004 |
| WO | 2005000382 A3 | 1/2005 |
| WO | 2007015232 A1 | 2/2007 |
| WO | 2007091671 A1 | 8/2007 |
| WO | 2008147117 A2 | 4/2008 |
| WO | 2008080109 A1 | 7/2008 |
| WO | 2008081444 A2 | 7/2008 |
| WO | 2009023798 A2 | 2/2009 |
| WO | 2009070657 A2 | 6/2009 |
| WO | 2009145447 A1 | 12/2009 |
| WO | 2010085059 A2 | 7/2010 |
| WO | 2011039728 A1 | 4/2011 |
| WO | 2011093674 A2 | 8/2011 |
| WO | 2012057425 A1 | 5/2012 |
| WO | 2012077943 A2 | 6/2012 |
| WO | 2012140643 A1 | 10/2012 |
| WO | 2013180422 A1 | 12/2013 |
| WO | 2014004644 A1 | 1/2014 |
| WO | 2014110016 A1 | 7/2014 |
| WO | 2014151104 A1 | 9/2014 |
| WO | 2015119376 A1 | 8/2015 |
| WO | 2015163731 A1 | 10/2015 |
| WO | 2015188174 A1 | 12/2015 |
| WO | 2016022865 A1 | 2/2016 |

OTHER PUBLICATIONS

Yan et al, Enhancing DNA Delivery into the Skin with a Motorized Microneedle, European Journal of Pharmaceutical Sciences 52 (2014) 215-222, 8 pgs.

Bomtech Electronics Co. Ltd. Motorized Micro Needle Therapy, http://bomtech.net/product/medical_8.htm, 1 pg.

Dermapen, Retrieved on Aug. 29, 2016 from http://dermapen.com/dermapen/, 2 pages.

BeautyPen, Retrived on Aug. 29, 2016 from http://www.ibeautymachine.com/motorized-micro-needle-system-12-needle-rechargeable.html, 20 pages.

Eclipse MicroPen, Retrieved on Aug. 29, 2016 from http://www.eclipsemicropen.com/about/eclipse-micropen/, 7 pages.

* cited by examiner

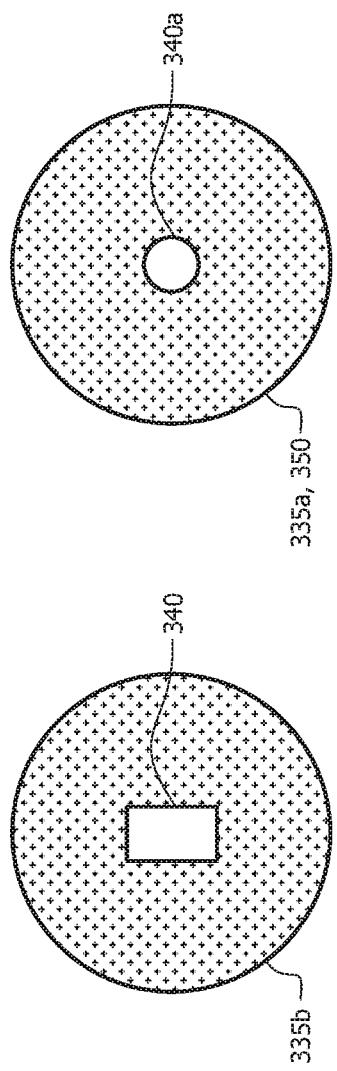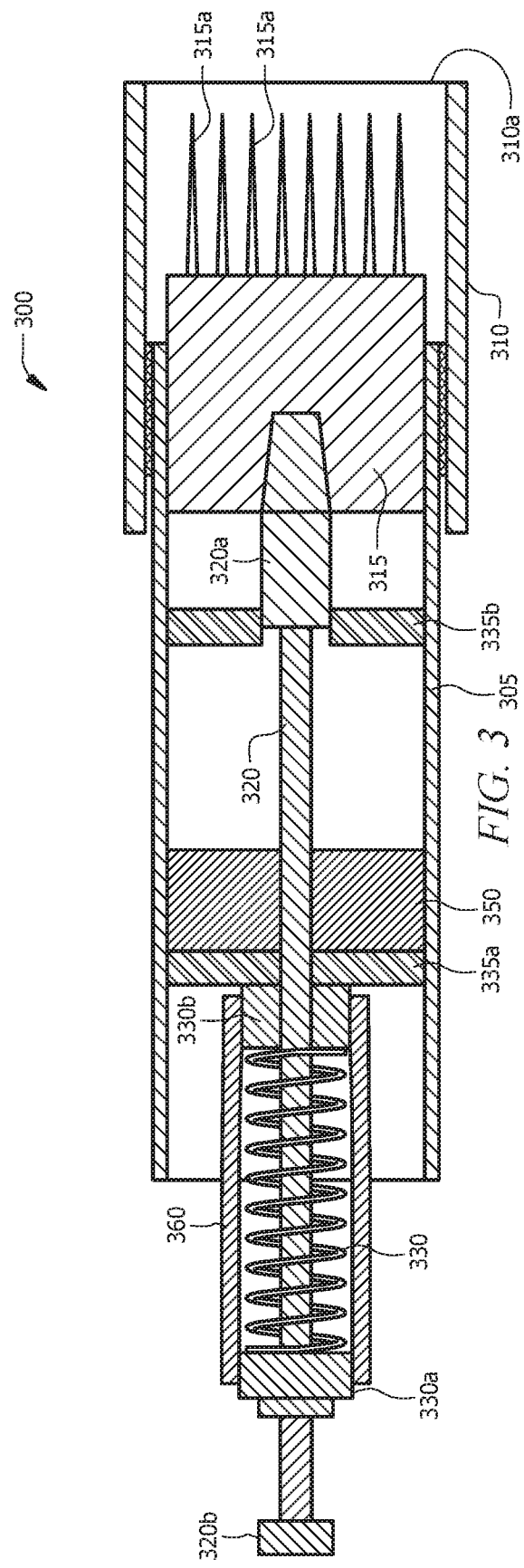
*FIG. 3A*
*FIG. 3B*
*FIG. 3*

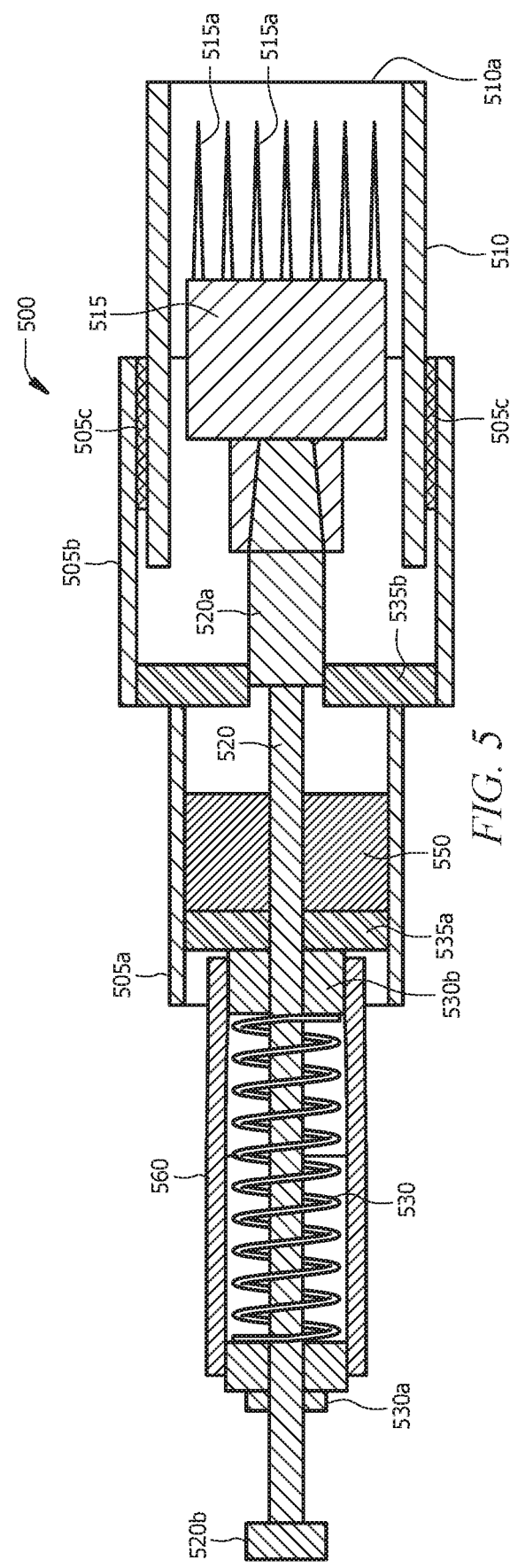
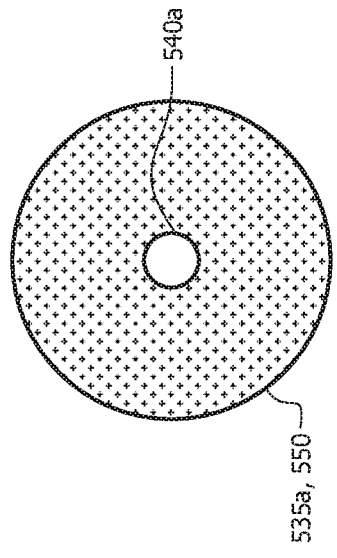
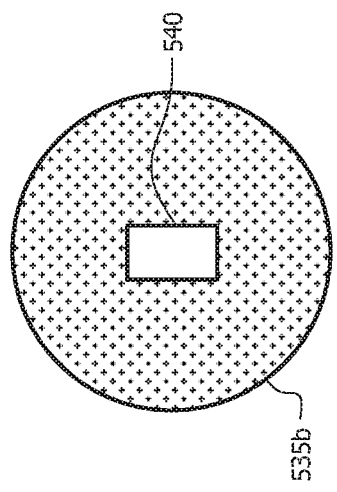

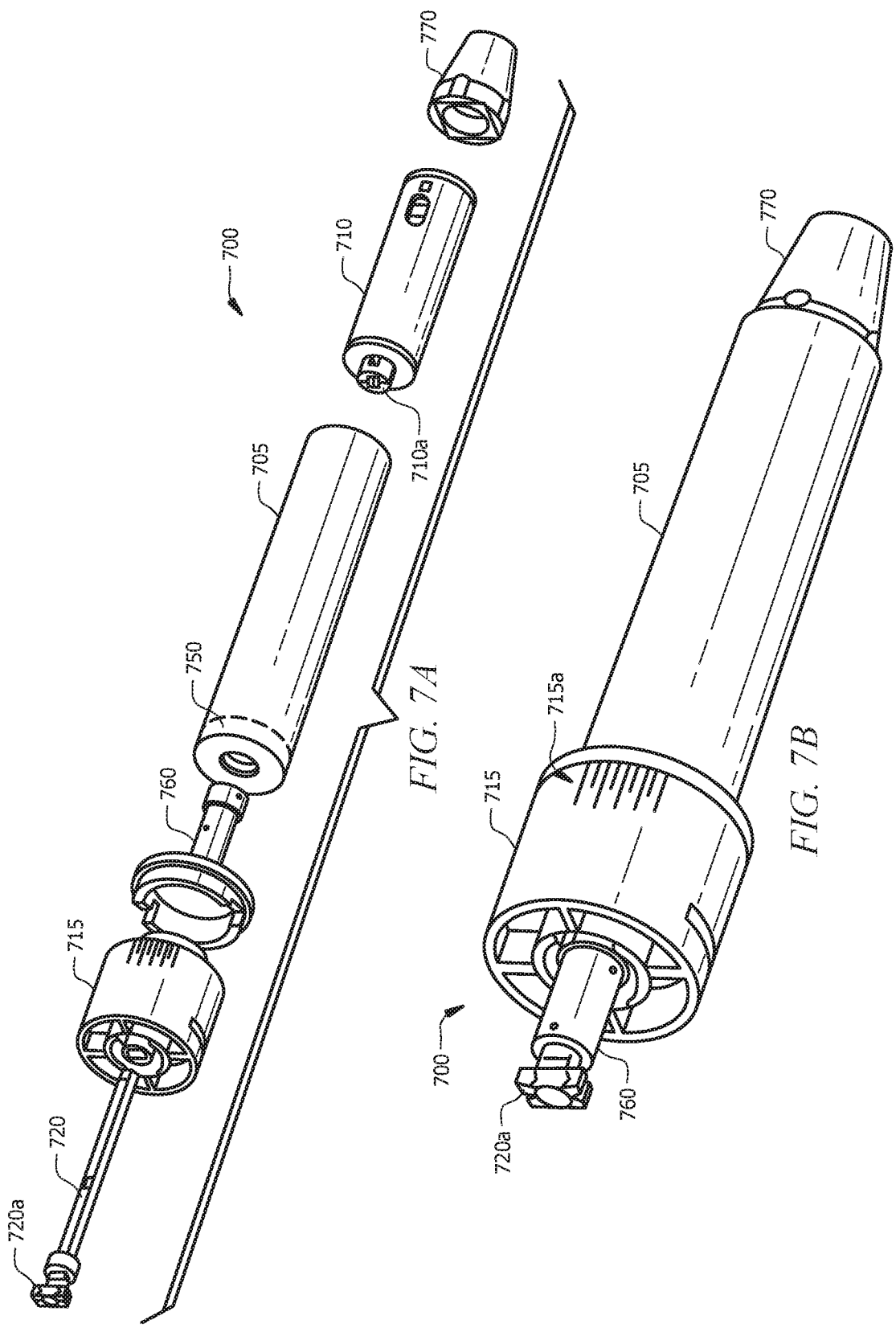

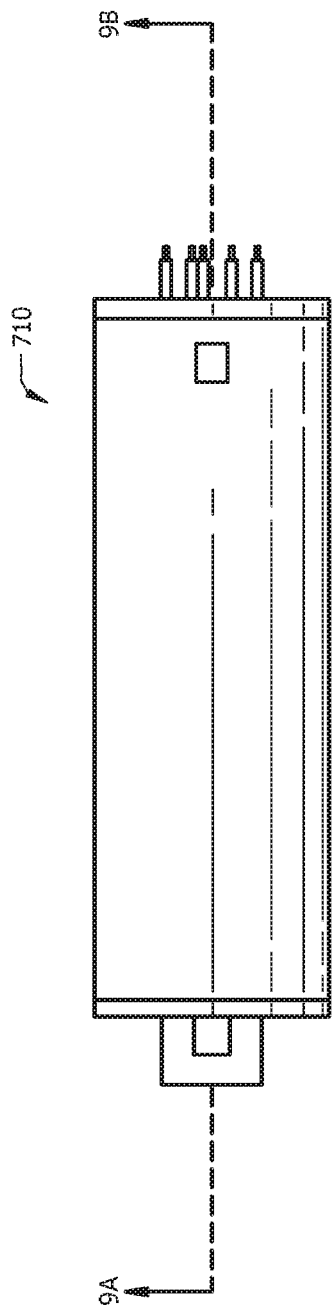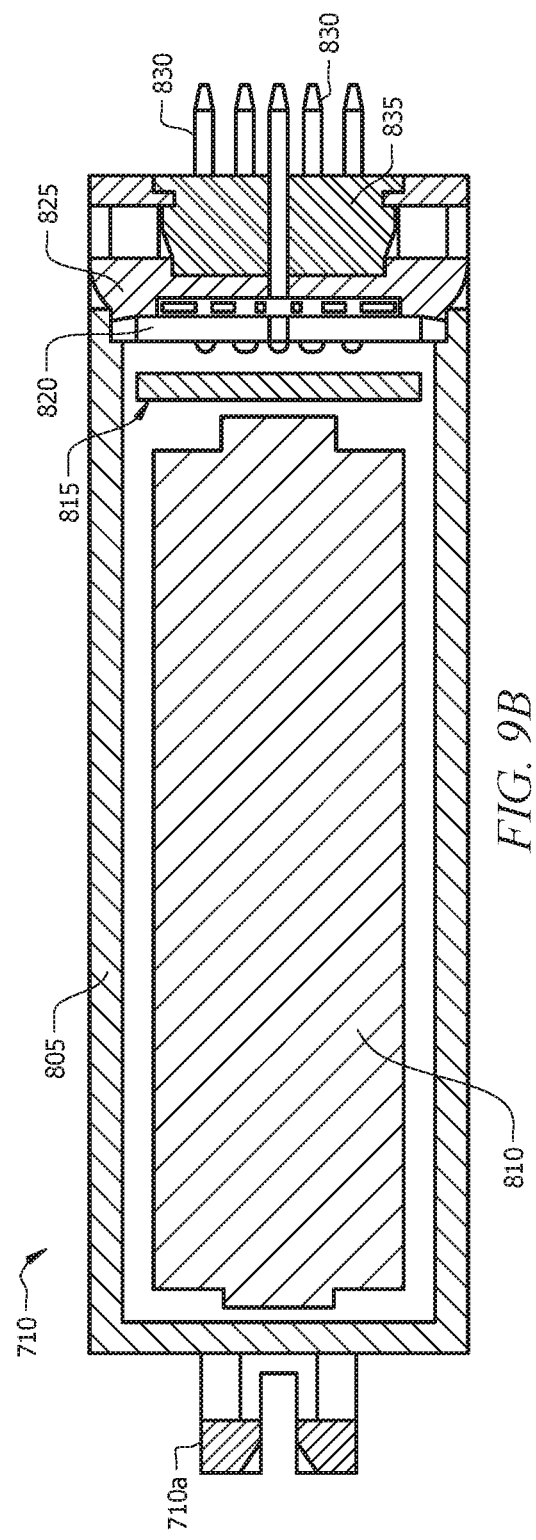
FIG. 9A
FIG. 9B

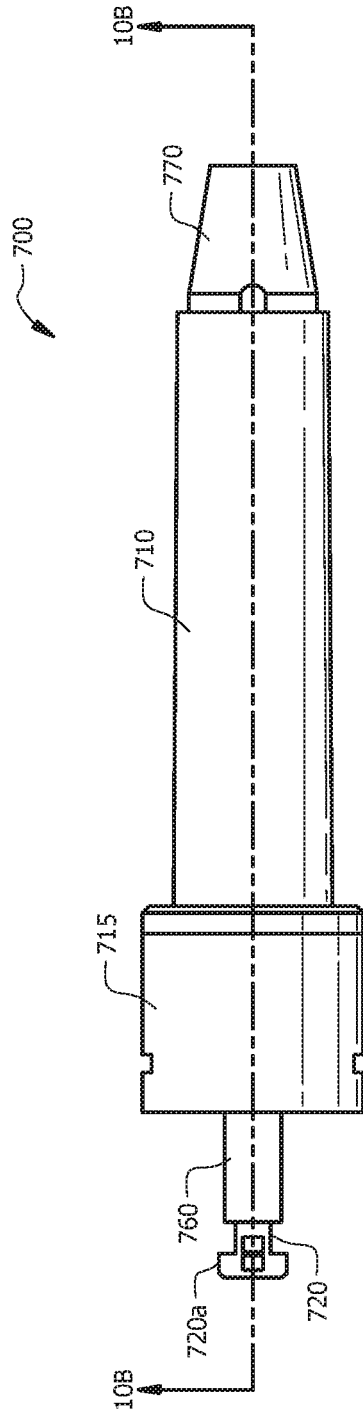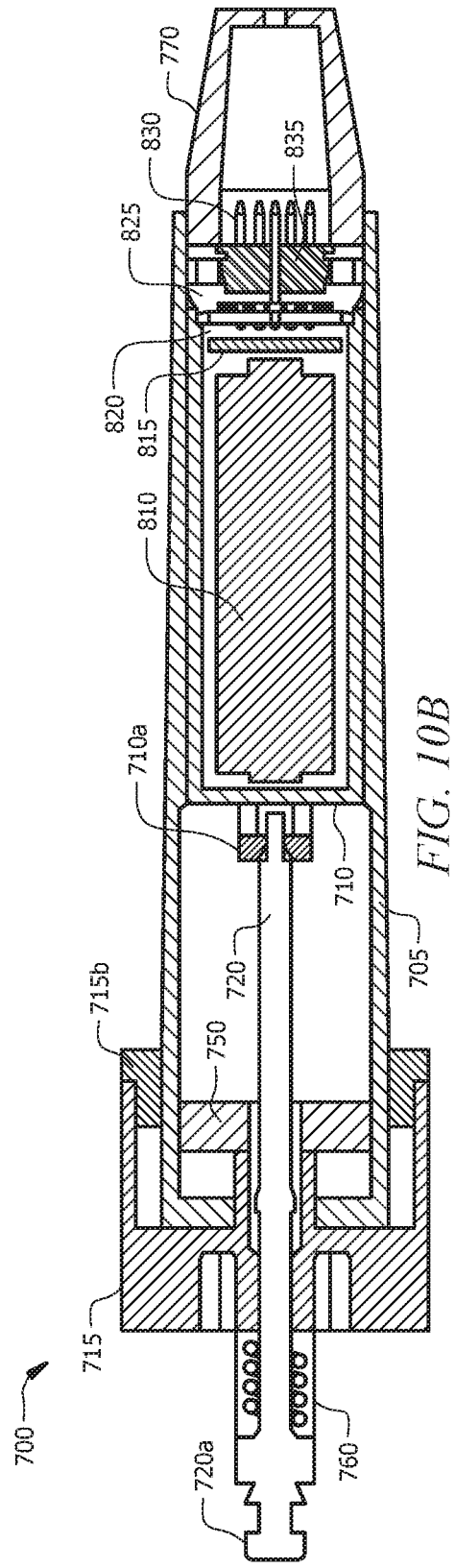

NEEDLING DEVICE FOR USE WITH DISPOSABLE NEEDLE CARTRIDGES

CROSS-REFERENCE TO RELATED APPLICATION

This application is a continuation of, and thus claims priority to, U.S. patent application Ser. No. 15/495,564, filed Apr. 24, 2017, which is a continuation-in-part application of U.S. patent application Ser. No. 15/356,079, filed Nov. 18, 2016, which is a continuation-in-part application of U.S. patent application Ser. No. 15/176,223, filed Jun. 8, 2016, each of which are hereby incorporated by reference in their entirety for all purposes.

TECHNICAL FIELD

The present disclosure relates to dermatological microneedling apparatuses, and in particular to dermatological microneedling apparatuses that provides for use of disposable needle cartridges at an angular offset.

BACKGROUND

Typically, dermatological microneedling apparatuses indicate apparatuses that are used in an aesthetic transdermal procedure that involves repeatedly puncturing the skin with tiny, sterile needles (so-called "microneedling" the skin). In addition, many liquid injection apparatuses include those microneedling procedures performed for injecting a tattooing pigment or liquid/gel medicine, collagen or other items, into the skin or in an affected area of the skin for aesthetic purposes. Such microneedling apparatuses typically includes a needle cartridge having one or more needles therein, where the entire needle cartridge is disposable in order to prevent contamination from one patient to another. To accomplish this, such apparatuses provide for a detachable needle cartridge that include a needle unit and which mount to the front end of the microneedling apparatus during use.

However, although conventional microneedling apparatuses use disposable needle cartridges, blood and other liquids oozing out of the skin during use of the apparatus on a patient frequently flows into a (re-useable) main body of the microneedling apparatus along the disposable needle cartridge during a procedure. In early apparatuses, only a mechanical connection between a needle unit or cartridge and the main body existed, which could not block the small amount of the blood (or other liquids) flowing back into the apparatus body from the needle unit or cartridge, and therefore the blood or other contaminating liquids of the previously operated person remained in the main body after the liquid injection apparatus was used, even if the needle unit or cartridge were replaced before the next patient. This resulted in an unacceptable risk of contaminating the next patient with the blood or other liquids from the prior patient.

In newer conventional apparatuses, seals have been employed within the disposable needle cartridge in an attempt to either block contaminating fluids from flowing back into the main body of the device, or to capture such fluids flowing back through the needle cartridge. Such an exemplary attempt may be seen in U.S. Pat. No. 8,920,379 to Lee. Unfortunately, these needle cartridges rely on attempting to hermetically seal the components of the needle cartridge from the main body of the microneedling device or "pen." But even the implementation of seals that are intended to be airtight, the "sealed" cartridges still cannot thoroughly prevent contaminants flowing back into the main body of the apparatus. For example, with the Lee design in the '379 patent, the rubber material employed to provide seals between the needle unit and the reciprocating shaft that moves the needle unit in and out during use of the apparatus still allows the leaking of some fluids from the cartridge to the main body of the apparatus. Such leaking is caused by the quick movement of the components the sealing member is intended to hermetically grasp during use of the apparatus, and thus maintaining an airtight seal on such quickly moving components has proven to be troublesome, if not impossible. Accordingly, even with these new designs attempting to create airtight seals between the cartridge and the main body of the pen device, it has proven difficult for such conventional liquid injection devices to completely block liquid contaminants from flowing back into the main body of the apparatus, which then contaminate the new needle cartridge employed for the next person.

Accordingly, there is a need in the art for a disposable needle cartridge that can more effectively block liquid contaminants from flowing back through the cartridge and contaminating the main body of the apparatus, but which does not suffer from the deficiencies of the prior art mentioned above. The present disclosure provides such solutions.

SUMMARY

To overcome the deficiencies of the prior art, the disclosed principles provide for various embodiments of dermatological microneedling devices, including liquid injection devices, for use with disposable needle cartridges. Some embodiments may also include an absorbing barrier that prevents liquid contaminants from flowing back through the cartridge and reaching the main body of the device. In one embodiment, such a microneedling device may comprise a main body having a front end and a back end opposite its front end, the main body comprising a drive motor, drive circuitry for controlling the drive motor, and a drive linkage located on a distal end of the drive motor rotor. Such a microneedling device may also comprise a power source capsule having a proximal end coupled to the back end of the main body, the power source capsule comprising a power source and associated power source management circuitry. Also included may be a needle cartridge having a proximal end coupled to the front end of the main body, where the needle cartridge comprises a drive shaft disposed therethrough, and a needle unit coupled to a distal end of the drive shaft to move therewith, the needle unit having at least one needle extending therefrom. In such embodiments, the drive shaft comprises a linkage member configured to engage the drive linkage of the drive motor, and is configured to be driven by the drive motor and thereby drive movement of the needle unit such that the at least one needle extends beyond and retracts within the distal end of the needle cartridge. Additional examples may include an the microneedling device with RF energy circuitry powered by the power source and configured to generate RF energy, as well as transfer circuitry configured to transfer the generated RF energy from the RF energy circuitry to the at least one needle.

In another embodiment, a transdermal microneedling apparatus may comprise a main body having a front end and a back end opposite its front end, where the main body comprises a drive motor, drive circuitry for controlling the drive motor, and a drive linkage located on a distal end of the drive motor rotor. Such an apparatus may also include a power source capsule having a proximal end coupled to the back end of the main body, where the power source capsule comprises a power source and associated power source management circuitry. A needle cartridge removably coupled to the main body at an angle or angular offset may also be included on the device. Such an exemplary needle cartridge may comprise a drive shaft disposed therethrough, and a needle unit coupled to a distal end of the drive shaft to move therewith, where the needle unit has at least one needle extending therefrom and a fluid reservoir configured to hold a liquid for dispensing via the at least one needle. In such exemplary embodiments, the drive shaft comprises a linkage member configured to engage the drive linkage of the drive motor, and is configured to be driven reciprocally along a longitudinal axis of the needle cartridge by the linkage member and drive linkage, and thereby move the needle unit reciprocally along the longitudinal axis of the needle cartridge such that the at least one needle extends beyond and retracts within the distal end of the needle cartridge. In at least one example, the drive linkage may include an angular drive. The needle cartridge may also include a spring configured to compress when the drive shaft longitudinally moves in a first direction from the proximal end of the needle cartridge to the distal end of the needle cartridge, and to expand to move the drive shaft back in a second direction opposite to the first direction Additional examples may include an RF microneedling device may also include RF energy circuitry at least partially housed in the main body and configured to be powered by the power source to generate RF energy, as well as transfer circuitry configured to transfer the generated RF energy from the RF energy circuitry to the at least one needle, and comprising one or more electrical interconnections between the RF energy circuitry and the at least one needle.

BRIEF DESCRIPTION OF THE DRAWINGS

The detailed description that follows, by way of non-limiting examples of embodiments, makes reference to the noted drawings in which reference numerals represent the same parts throughout the several views of the drawings, and in which:

FIG. 3 illustrates a cross-sectional side view of another embodiment of a disposable needle cartridge constructed in accordance with the disclosed principles;

FIG. 3A illustrates a top view of an exemplary shape for one of the support members in the embodiment of the disposable needle cartridge illustrated in FIG. 3;

FIG. 3B illustrates a top view of an exemplary shape for another of the support members and/or the absorbing member in the embodiment of the disposable needle cartridge illustrated in FIG. 3;

FIG. 5 illustrates a cross-sectional side view of yet another embodiment of a disposable needle cartridge constructed in accordance with the disclosed principles;

FIG. 5A illustrates a top view of an exemplary shape for one of the support members in the embodiment of the disposable needle cartridge illustrated in FIG. 5;

FIG. 5B illustrates a top view of an exemplary shape for another of the support members and/or the absorbing member in the embodiment of the disposable needle cartridge illustrated in FIG. 5;

FIG. 7A illustrates an exploded view of an embodiment of an RF energy emitting disposable needle cartridge in accordance with the disclosed principles;

FIG. 7B illustrates an isometric view of the embodiment of the RF energy emitting disposable needle cartridge of FIG. 7A in an assembled state;

FIG. 9A illustrates a side view the RF needle capsule illustrated in FIG. 8A and FIG. 8B in an assembled state;

FIG. 9B illustrates a cross-sectional side view of the RF needle capsule illustrated in FIG. 9A.

FIG. 10A illustrates a side view of the disposable RF needle cartridge illustrated in FIG. 7A and FIG. 7B in an assembled state;

FIG. 10B illustrates a cross-sectional side view of the RF needle cartridge illustrated in FIG. 10A;

DETAILED DESCRIPTION

In view of the foregoing, through one or more various aspects, embodiments and/or specific features or sub-components, the present disclosure is thus intended to bring out one or more of the advantages that will be evident from the description. The present disclosure makes reference to one or more specific embodiments by way of illustration and example. It is understood, therefore, that the terminology, examples, drawings and embodiments are illustrative and are not intended to limit the scope of the disclosure.

Figure 1:
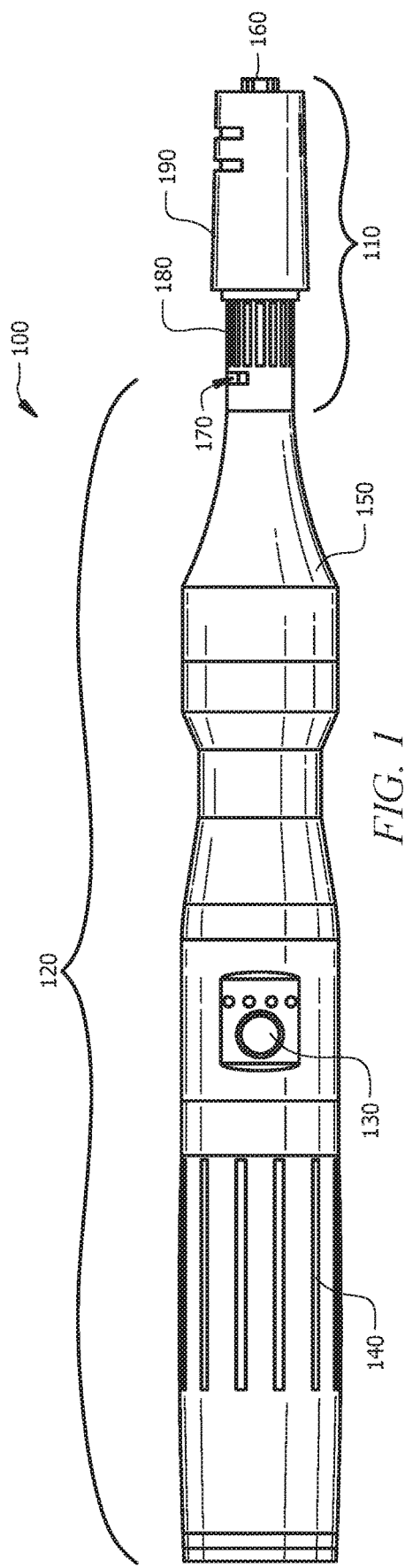
FIG. 1 illustrates an external side view of one embodiment of a microneedling apparatus that includes a disposable needle cartridge constructed in accordance with the disclosed principles.

FIG. 1 illustrates an external side view of one embodiment of a microneedling apparatus or device 100 (which may also be referred to as a "pen") that includes a disposable needle cartridge 110 constructed in accordance with the disclosed principles. The device 100 includes a main body 120 that houses the electric motor and associated circuitry, and externally includes one or more buttons 130 for ON/OFF operation of the device 100 as well as optional speed control depending on the model of device 100. The main body 120 also includes a handle area 140, which may include a textured surface for better gripping by a user during use of the device 100.

On the end of the main body 120 opposite the handle area 140, the device includes a front housing 150. The front housing 150 conceals the cam system that translates the spinning of the electric motor within the main body 120 into the reciprocating "in and out" motion used to drive the needle unit 160 housed within the needle cartridge 110. Accordingly, the front housing 150 may be removable from the remainder of the main body 120 in order to service the cam system, if needed. Additionally, the front housing 150 includes one or more attachment features 170 on its distal end which are configured to removably couple the needle cartridge 110 to the main body 120 of the device 100. Such attached feature(s) 170 may be any type of attachment configuration, such as the snap-fit type illustrated, or may even be threaded if desired.

The disposable needle cartridge 110 itself includes a base portion 180 on a proximal end, which is coupled to the main body 120, and the needle unit 160 on its distal end. The inner workings of the needle cartridge 110, which are not visible from this external view of the microneedling device 100, will be described in detail below. The needle cartridge 110 also includes a depth adjustment sleeve 190 movably coupled to a distal end of the base portion 180. In an advantageous embodiment, the depth adjustment sleeve 190 includes internal threads on the end proximal to the main body 120, while the distal end of the base portion 180 includes corresponding threads. With this type of threaded engagement between the depth adjustment sleeve 190 and the base portion 180 of the cartridge 110, the sleeve 190 may be rotated about the longitudinal axis of the device 100 to change its longitudinal distance with respect to the device 100. As the sleeve 190 moves closer to or farther from the main body 120, the needles of the needle unit 160 become more or less exposed, respectively, from within the sleeve 190. This allows a user to "dial in" the desired depth that the needles pierce the skin of a patient when the distal end of the sleeve 190 is pressed against the patient's skin during use of the device 100.

Moreover, the pitch of the threads connecting the sleeve 190 to the base portion 180 of the cartridge 110 may be selected fine enough such that very precise depth control of the needles is provided. Also, by providing needle depth control via the externally located sleeve 190, as opposed to conventional devices that provide needle depth control by actually adjusting the distance of the needle unit from the main body 120, not only is the disclosed depth adjustment system far less complex, but it is also far more precise since little to no play between the depth adjustment components exists. Thus, the disclosed depth adjustment system is not only more precise, but its more simplistic design greatly reduces manufacturing costs as compared to such conventional systems, as well as potential service or repair costs should such conventional systems fail.

Figure 2A:
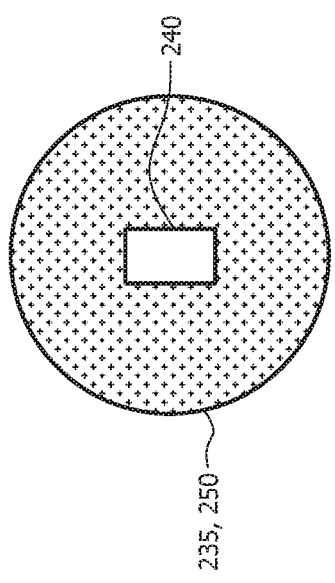
FIG. 2A illustrates a top view of an exemplary shape for the support members and absorbing members in the embodiment of the disposable needle cartridge illustrated in FIG. 2.
Figure 2:
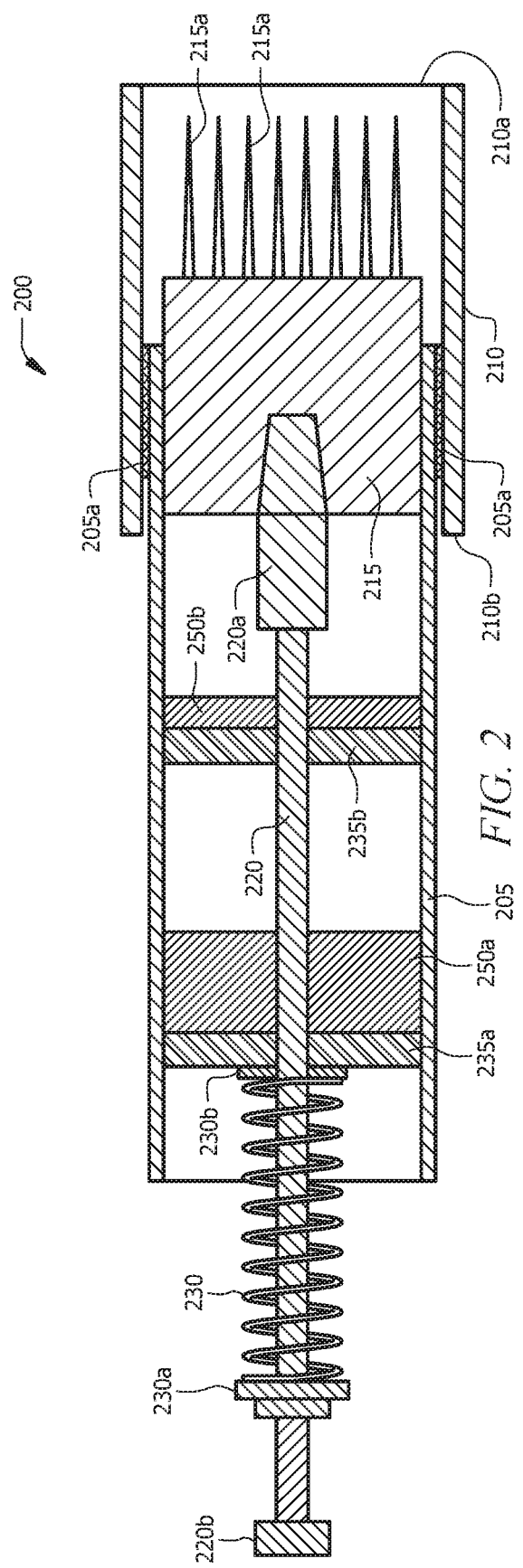
FIG. 2 illustrates a cross-sectional side view of one embodiment of a disposable needle cartridge constructed in accordance with the disclosed principles.

FIG. 2 illustrates a cross-sectional side view of one embodiment of a disposable needle cartridge 200 constructed in accordance with the disclosed principles. The needle cartridge 200 again includes a base portion 205, as well as a depth adjustment sleeve 210 and a needle unit 215. In this embodiment, the depth adjustment sleeve 210 is rotationally coupled to the base portion 205 using threads 205a. As discussed above, the threaded attachment of the depth adjustment sleeve 210 to the base portion 205 allows a user to precisely adjust the maximum distance the needles 215a of the needle unit 215 will longitudinally extend beyond the distal end 210a of the depth adjustment sleeve 210. Moreover, a graduation scale (not illustrated) may be included on the external surface of the base portion 205 such that the proximal end 210b of the sleeve 210 aligns with graduations indicating to a user the specific maximum distance the needles 215a will extend beyond the distal end 210a of the sleeve 210 during use of the injection device to which the cartridge 200 is attached. Also as discussed above, the means by which the depth adjustment sleeve 210 is movably coupled to the base portion 205 may be different than the illustrated threaded attachment means, such as a sliding mechanism, while still falling within the broad scope of the present disclosure.

The needle cartridge 200 also includes a reciprocating drive shaft 220 passing through the base portion 205 and attaching to the needle unit 215. In the illustrated embodiment, the drive shaft 220 is connected to the needle unit 215 using a threaded end 220a, but any type of attachment means for connecting the drive shaft 220 to the needle unit 215 may also be employed within the broad scope of the disclosed principles. On a proximal end of the drive shaft 220 is a shaft cam member 220b configured to engage a corresponding drive motor cam member (not illustrated). As discussed above with the embodiment illustrated in FIG. 1, a drive motor within the main body of a microneedling device on which the disposable cartridge 200 includes a rotor shaft that rotates during operation of the injection device. The distal end of the rotor shaft is attached to the drive motor cam member such that it is rotated by the drive motor.

Within the cam mechanism, the rotation of the drive motor cam member is translated to the shaft cam member 220b such that the shaft cam member 220b is moved in and out longitudinally with respect the injection device. The cam mechanism can accomplish this simply by providing high and low surfaces within the drive motor cam member that contact the bottom surface of the shaft cam member 220b when it rotates. During this rotation, as the protruding high surfaces come into contact with the shaft cam member 220b, the drive shaft 220 is pushed away from the drive motor cam member. Conversely, once the high surface no longer are in contact with the shaft cam member 220b, a coil spring 230 is used to push the drive shaft 220 back towards the main body of the microneedling device such that the shaft cam member 220b now contacts the low, non-protruding surfaces of the drive motor cam member. Then, once again as the shaft cam member 220b encounters a high, protruding surface of the drive motor cam member, the shaft cam member 220b, and thus the drive shaft 220, is again push away from the main body of the microneedling device, which in turn compresses the coil spring 230 so that it may provide the force needed to push the drive shaft 220 back towards the device when needed.

Each time the cam mechanism causes the drive shaft 220 to move away and towards the main body of the microneedling device, the reciprocal drive shaft 220, which is affixed to the base of the needle unit 215, causes the needle unit 215 to correspondingly reciprocate away and towards the injection device within both the base portion 205 and the sleeve 210. It should be noted, of course, that any other type of mechanism used to translate the rotation of the drive motor's shaft to the reciprocating motion of the drive shaft 220 may also be employed with a disposable cartridge 200 according to the disclosed principles, and thus the discussed embodiment is merely exemplary. Consequently, when the distal end 210a of the sleeve 210 is held against the surface of the skin, this in and out movement of the needle unit 215 within the sleeve in turn causes the needles 215a to be extended beyond and be retracted within, respectively, the distal end 210a of the depth sleeve 210. This continuous extension beyond and retraction within the sleeve 210 is what provides the piercing or scratching of the skin by the needles 215a of the needle unit during use of the cartridge 200 during a microneedling procedure. In embodiments where the cartridge is used in a liquid injection microneedling procedure, injection of the liquid or other substance (e.g., from a fluid reservoir in the needle unit 215 and up through a plurality of liquid discharge holes at the base of the needles 215a) into a patient's skin.

The base portion 205 further includes therein one or more support members, which in this illustrated embodiment comprise two support members 235a, 235b. These support members 235a, 235b may be affixed to the interior of the base portion 205 to provide centering guides for the reciprocating drive shaft 220. Also, a first support member 235a may also provide a distal bearing surface 230b for a distal end of the coil spring 230, while a proximal bearing surface 230a for the coil spring 230 may be provide at an advantageous location on the drive shaft 220 itself. These bearing surfaces 230a, 230b allow the coil spring 230 to compress when the drive shaft 220 is moving outwardly, as well as provide the surfaces the compressed spring 230 pushes against to move the drive shaft 220 back inwardly during its reciprocating motion.

Moreover, these support members 235a, 235b may include a rectilinear aperture for the drive shaft 220 to pass through in embodiments where the drive shaft 220 has a corresponding rectilinear cross-section. Looking briefly at FIG. 2A, illustrated is a top view of an exemplary shape for the support members 235a, 235b. Specifically, to assist in preventing the drive shaft 220 from rotating as it reciprocates within the base portion 205, the cross-section of the drive shaft 220 may be non-circular in shape. The support members 235a, 235b may then each include an aperture 240 having a corresponding shape to the cross-section of the drive shaft 220, which would thus allow the drive shaft 220 to reciprocally (longitudinally) move through the support members 235a, 235b but prevent the drive shaft 220 from rotating as well. In the illustrated embodiment, the aperture 240 is shown as rectangular in shape, but any other non-circular shape, such as a square, triangle or any other non-circular shape, may instead be employed with the cross-section of the drive shaft 220 have a corresponding shape. Also, the attachment end 220a affixed to the needle unit 215, which may even be an extending base portion of the needle unit 215 itself that receives the end of the drive shaft 220 therein, may have the non-circular shape that passes through the aperture(s) while the drive shaft 220 maintains a typical round shape. In such embodiments, the non-circular attachment end or extending base portion of the needle unit would still assist in preventing rotation of the drive shaft as the drive shaft and needle unit reciprocate longitudinally. Such an embodiment is discussed with reference to FIGS. 3 and 3A below.

Returning to FIG. 2, the base portion 205 further includes one or more absorbing members that prevent patient blood and liquid mixture to be injected in the patient's skin from passing from the needle unit 215 through the base portion 205, and back into the main body of the microneedling device. Specifically, the absorbing members, which in this exemplary embodiment comprise two absorbing members 250a, 250b, are sized so that their external diameters contact the interior surface of the base portion 205, and their internal diameters contact the drive shaft 220. Moreover, in this embodiment, the absorbing members 250a, 250b each rest against one of the corresponding support members 235a, 235b. The absorbing members 250a, 250b are provided within a disposable needle cartridge 200 designed and constructed in accordance with the disclosed principles as a fluid barrier to prevent the backflow of blood discharged from the skin of a patient, as well as any injection liquid mixture, that may flow from the needle unit through the base portion 205 and back to the main body of the injection device during a medical procedure. Thus, the disclosed principles, rather than simply attempting to seal the cartridge from the main body of the microneedling device actually provides absorbing members to soak up and hold any such fluids that would otherwise backflow through the needle cartridge. Turning back briefly to FIG. 2A, the absorbing members 250a, 250b may also be formed with a non-circular shaped aperture 240 in those embodiments where the support members 235a, 235b also have a corresponding non-circular shape. Of course, if a drive shaft 220 with a circular cross-section is employed, both the support members 235a, 235b and absorbing members 250a, 250b may have corresponding circular apertures.

Moreover, multiple absorbing members may be employed in accordance with this technique, such as the illustrated use of two absorbing members 250a, 250b in FIG. 2. Furthermore, each such multiple absorbing member may be made in different sizes or thicknesses, also as provided in the exemplary embodiment of FIG. 2. The material used to form the absorbing members maybe any suitable material capable of absorbing these fluids, which could be an organic material such as cotton or even a synthetic material. Importantly, seals provided in needle cartridges typically need to be of a flexible nature for maximum effectiveness, and thus this limitation can create a "shelf life" for a needle cartridge only employing such seal material. More specifically, rubber or other similar material typically used for seals will dry out (i.e., "dry rot") over time, and thus it would be difficult for a user of such a needle cartridge to determine if the seal/seal material is still intact before use. In contrast, because the disclosed principles provide for an absorbing fluid barrier, as a needle cartridge with such a barrier sits over time, the absorbing members would not be at risk of drying out, and thus would maintain their ability to absorb indefinitely. As a result, a user could confidently use a needle cartridge as disclosed herein without risk that the fluid barrier has deteriorated.

Also, by providing a liquid or fluid barrier within a needle cartridge that absorbs substances rather than simply providing a seal against the backflow of such substances, the disclosed principles provide the further advantage that such backflowing liquids are also less likely to leak from the needle cartridge 200 once the cartridge is removed from the microneedling device. With conventional needle cartridges that simply provide seals, the backflowing liquids often still flow within the cartridge, and thus could leak from the needle unit end of the cartridge either while it is still attached to the microneedling device, or even after it has been removed. Such continued risk of flowing from a different area of the needle cartridge presents another unnecessary contamination risk beyond preventing backflow to the microneedling device. By providing a liquid barrier that is an absorption barrier rather than simply a seal, such continued risk of contamination is also eliminated. Moreover, the disclosed absorption barrier technique may even be combined with the use of one or more seals if desired.

Looking now at FIG. 3, illustrated is a cross-sectional side view of another embodiment of a disposable needle cartridge 300 constructed in accordance with the disclosed principles. This embodiment of the needle cartridge 300 again includes a base portion 305, as well as a depth adjustment sleeve 310 and a needle unit 315. In addition, this embodiment includes a drive shaft 320 passing through the base portion 305 and attached to the base of the needle unit 315 using an attachment member 320a also attached to the drive shaft. The opposing, proximal end of the drive shaft 320 (proximal again with respect to the microneedling device on which the cartridge 300 is mounted) again includes a cam member 320b for use in translating the rotation of a drive motor in the microneedling device (not illustrated) into longitudinal reciprocating motion of the drive shaft 320, as discussed in detail above.

This embodiment of the disposable needle cartridge 300 again includes a coil spring 330 for pushing the drive shaft 320 back towards the main body of a microneedling device to which the needle cartridge 300 is attached to assist with the reciprocating motion of the drive shaft 320. The coil spring 330 again sits between first and second bearing surfaces 330a, 330b that cause the coil spring 330 to compress when the drive shaft 320 is moving outwardly, as well as provide the surfaces the compressed spring 330 pushes against to move the drive shaft 320 back inwardly towards the microneedling device during its reciprocating motion. Also, this alternative embodiment includes a single absorbing member 350 that provides a liquid barrier in accordance with the disclosed principles. Accordingly, the absorbing member 350 may be comprised of an absorbing material such as cotton to prevent patient blood and/or liquid mixture being injected in the patient's skin from passing from the needle unit 315 through the base portion 305, and back into the main body of the microneedling device holding the needle cartridge 300. Thus, as before, the absorbing member 350 may be sized so that its external diameter contacts the interior surface of the base portion 305, and its internal diameter contacts the drive shaft 320. Moreover, the absorbing member 350 may be located so that it rests against one of the support members 335a, helping to keep it in position.

In addition, however, this embodiment of the disposable needle cartridge 300 now includes a seal member 360 attached to the outer surfaces of the bearing members 330a, 330b. More specifically, in this embodiment, a distal end of the seal member 360 is sealed to the second bearing member 330b, which in turn is sealed against (by being coupled to or simply formed with) the first support member 335a, which in turn is sealed against (again, by being coupled to or simply formed with) the inner surface of the base portion 305. Thus, at this end of the seal member 360, backflowing liquid(s) would likely only pass through the area(s) between the drive shaft 320 and the aperture of the first support member 335a, which is sealed by the distal end of the seal member 360. Also, a proximal end of the seal member 360 is sealed to the first bearing member 330a, which in turn is sealed against the drive shaft 320. Thus, at this end of the seal member 360, backflowing liquid(s) would likely only pass over the first bearing member 330a, which is sealed by the proximal end of the seal member 360. Accordingly, the seal member 360 is provided at the base of the needle cartridge 300 as a further fluid/liquid barrier, in addition to the absorbing barrier provided by absorbing member 350, to further help prevent the backflow of blood discharged from the skin of a patient, as well as any injection liquid mixture in liquid injection application, that may flow from the needle unit 315 through the base portion 305 and back to the main body of the microneedling device during a medical procedure.

The material comprising the seal member 360 may be any advantageous material that may provide an airtight or hermetic seal. For example, the seal member 360 may be made from one or more natural rubber material(s), such as latex, isoprene, polyisoprene and other natural elastomers, as well as one or more synthetic rubbers materials, such as styrene-butadiene rubbers (SBR) and other petroleum-derived synthetic elastomers. Of course, no limitation to the materials used for the seal member 360, or combinations thereof, is intended or should be implied. Accordingly, although not required, such a seal may be combined with the unique absorbing barrier of the disclosed principles to provide a combined protection structure against backflowing liquids from the needle unit 315 to the main body of the microneedling device on which the disposable needle cartridge 300 is mounted.

Also in this embodiment, the second support member 335b is configured to receive a portion of the attachment member 320a therethrough as the drive shaft 320 moves inwardly and outwardly during use. Additionally, as in the illustrated embodiment, the external shape of the attachment member 320a may be formed with a non-circular shape. Likewise, the corresponding aperture 340, which may be seen looking momentarily at FIG. 3A, of the second support member 335b may be of the same non-circular shape. Thus, as the aperture 340 of the second support member 335b receives the attachment member 320a therethrough during reciprocating movement of the drive shaft 320, the corresponding non-circular shapes of these components assist in preventing the drive shaft 320 from rotating about the longitudinal axis of the cartridge 300. Although the non-circular shape of the aperture 340, as well as the corresponding external shape of the portion of the attachment end 320b received therein, are illustrated as rectangular, it should be understood that any non-circular shape may be employed within the broad scope of the disclosed principles. Looking briefly at FIG. 3B, illustrated is a top view of an exemplary shape for the first support member and/or the absorbing member 350 in this embodiment of the disposable needle cartridge 300. As illustrated, the aperture 340a of the first support member 335a and/or the absorbing member 350 may be circular in shape in embodiments where the cross-sectional shape of the drive shaft 320 is also circular. As discussed above, however, other corresponding shapes between apertures of the first support member 335a/absorbing member 350 and the drive shaft 320 may also be employed.

Figure 4A:
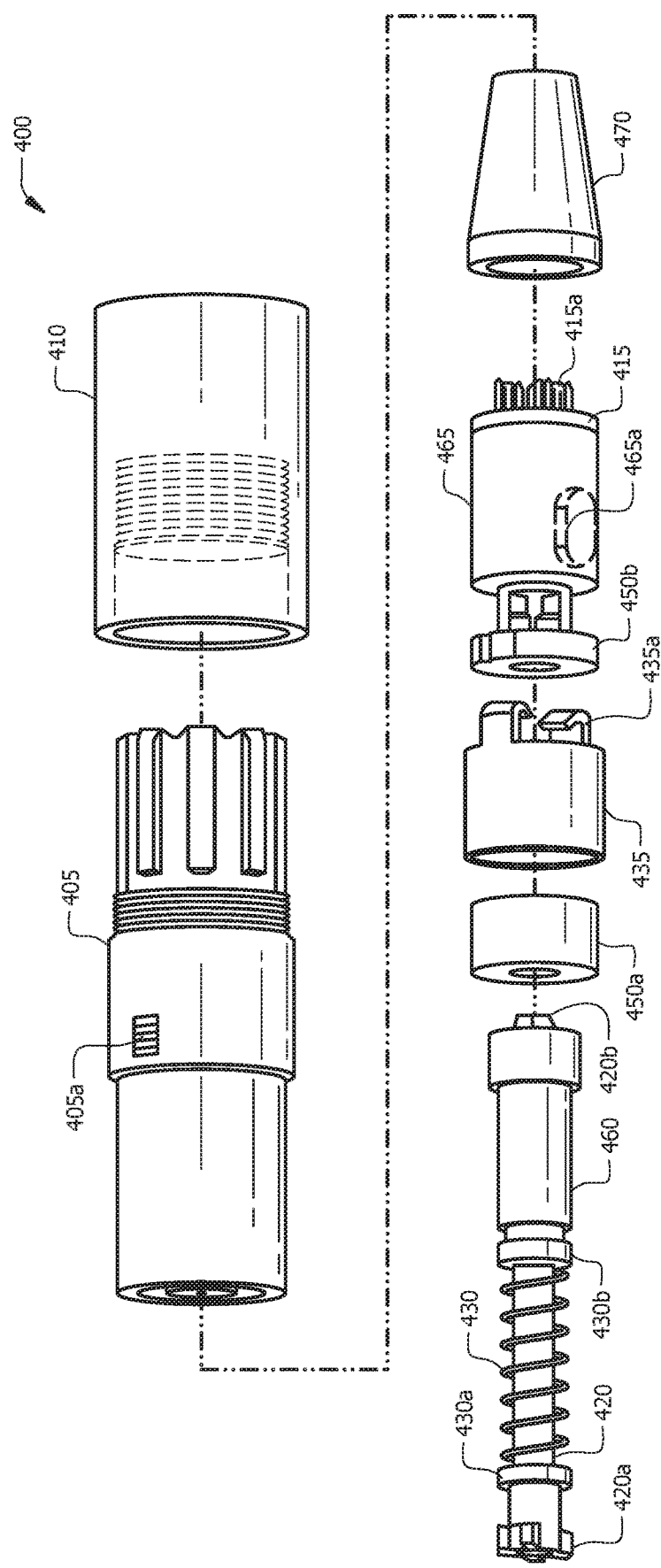
FIG. 4A illustrates an exploded side view of another embodiment of a disposable needle cartridge constructed in accordance with the disclosed principles.
Figure 4B:
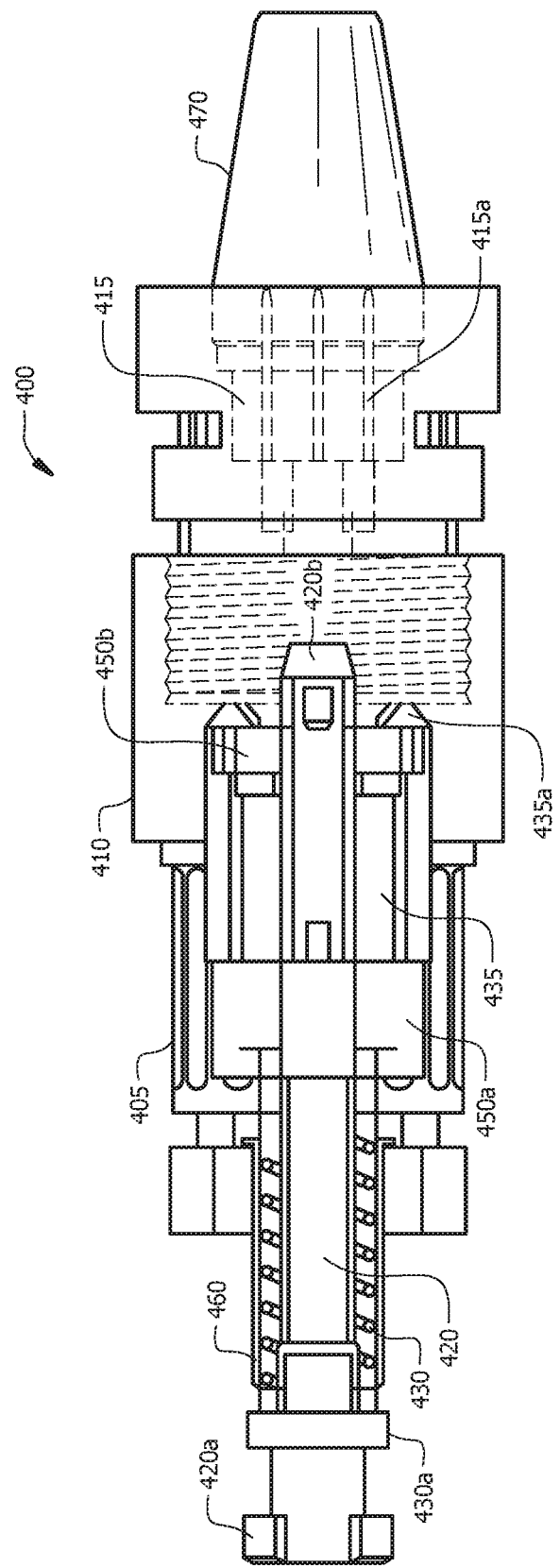
FIG. 4B illustrates a side, partially cross-sectional view of the embodiment of the disposable needle cartridge shown in FIG. 4A in an assembled state.

Turning now to FIG. 4A, illustrated is an exploded view of another embodiment of a disposable needle cartridge constructed in accordance with the disclosed principles. Additionally, FIG. 4B illustrates a side, partially cross-sectional view of the embodiment of the disposable needle cartridge 400 shown in FIG. 4A in an assembled state. This third embodiment of a needle cartridge 400 according to the disclosed principles again includes a base portion 405, as well as a depth adjustment sleeve 410 and a needle unit 415. In addition, this embodiment includes a drive shaft that will attached to the base of the needle unit 415 using an attachment end 420b of the drive shaft 420. The opposing, proximal end of the drive shaft 420 again includes a cam member 420a for use in translating the rotation of a drive motor in the microneedling device, which in this embodiment of the cartridge 400 is a liquid injection device (not illustrated), into longitudinal reciprocating motion of the drive shaft 420, as discussed above. Of course, the illustrated embodiment of the cartridge 400 may be used with a non-liquid injection microneedling apparatus as well.

This embodiment of the disposable needle cartridge 400 also again includes a coil spring 430 for pushing the drive shaft 420 back towards the main body of a microneedling liquid injection device to which the needle cartridge 400 is attached to assist with the reciprocating motion of the drive shaft 420. The coil spring 430 again sits between first and second bearing surfaces 430a, 430b that cause the coil spring 430 to compress when the drive shaft 420 is moving outwardly, as well as provide the surfaces the compressed spring 430 pushes against to move the drive shaft 420 back inwardly towards the injection device during its reciprocating motion. However, in this embodiment, the second bearing surface 430b is located at the base of a seal member 460. This seal member 460 is provided as a sealing sleeve 460 that is positioned over the drive shaft 420. In such embodiments, the seal sleeve 460 may be formed from a rigid or semi-rigid material, such as vulcanized rubber or plastic, or from soft material such as silicone. Moreover, the seal sleeve 460 may be formed partially of rigid materials, such as at the second bearing surface 430b to provide sufficient resiliency against the coil spring 430, and partially non-rigid materials that may provide better sealing properties against the drive shaft 420, such as any of the seal materials disclosed above with reference to FIG. 3.

Also, this embodiment includes a first and second absorbing members 450a, 450b that provides a further liquid barrier, and more accurately an absorbing barrier, as compared to the seal sleeve 460. Thus, as before, the absorbing members 450a, 450b may be comprised of an absorbing material such as cotton to prevent patient blood and liquid mixture being injected in the patient's skin from passing from the needle unit 415 through the base portion 405, and back into the main body of the microneedling device holding the needle cartridge 400. Also as before, the absorbing members 450a, 450b may be sized so that their external diameters contact the interior surface of the base portion 405, and their internal diameters contact the drive shaft 420. In such embodiments, the drive shaft 420 may have a circular cross-section, as illustrated, while the absorbing members 450a, 450b have corresponding circular shaped apertures therethrough. Alternatively, the drive shaft 420 or an attachment portion for the drive shaft 420 to the needle unit 415 may have a non-circular shape, with the absorbing members 450a, 450b having corresponding non-circular apertures, as discussed above. For this illustrated embodiment, the first absorbing member 450a is positioned between the distal end of the seal sleeve 460 and a single support member 435 size to contact the interior diameter of the base portion 405. Moreover, the support member 435 in this embodiment includes grasping features 435a use to hold the second absorbing member 450b in a desired position.

A liquid reservoir 465, which receives the needle unit 415 therein, may then rest directly on, or simply proximal to, the second absorbing member 450b. The reservoir 465 is used to hold the liquid(s) being injected into a patients skin during use of a liquid injection microneedling device holding the cartridge 400, and which may be dispensed into the reservoir 465 through a liquid dispensing aperture 465a. During use on a patient's skin, such as for tattooing or collagen injections, the liquid(s) pass through the needle unit 415 and onto the needles 415a extending beyond the depth adjusting sleeve 410. The threads used to position the depth sleeve 410 with respect to the base portion 405 may be seen in FIG. 4A, as well as the graduation scale 405a placed on the exterior surface of the base portion 405 that provides the user the precise maximum distance the needles 415a will extend beyond the depth adjustment sleeve 410 during use of the microneedling device. Finally, in this embodiment of a disposable needle cartridge 400 of the present invention, a protective cap 470 may also be provide to not only cover the needles 415a but also to provide a seal for liquids that may be present in the reservoir 465.

Referring now to FIG. 5, illustrated is a cross-sectional side view of yet another embodiment of a disposable needle cartridge 500 constructed in accordance with the disclosed principles. This embodiment of the needle cartridge 500 again includes a base portion 505, as well as a depth adjustment sleeve 510 and a needle unit 515. However, in this embodiment, the base portion is comprised of first base portion 505a and a second base portion 505b. As illustrated, the two base portions 505a, 505b may be manufactured with two different outer diameters. However, the two base portions 505a, 505b may still be manufactured as a single, integral piece, if desired.

As in other embodiments, this embodiment again includes a drive shaft 520 passing through the two base portions 505a, 505b and attached to the base of the needle unit 515 using an attachment member 520a also attached to the drive shaft. The opposing, proximal end of the drive shaft 520 (proximal again with respect to the microneedling device on which the cartridge 500 is mounted) again includes a cam member 520b for use in translating the rotation of a drive motor in the microneedling device (not illustrated) into longitudinal reciprocating motion of the drive shaft 520, as discussed in detail above.

This embodiment of the disposable needle cartridge 500 again includes a coil spring 530 for pushing the drive shaft 520 back towards the main body of a microneedling device to which the needle cartridge 500 is attached to assist with the reciprocating motion of the drive shaft 520. The coil spring 530 again sits between first and second bearing surfaces 530a, 530b that cause the coil spring 530 to compress when the drive shaft 520 is moving outwardly, as well as provide the surfaces the compressed spring 530 pushes against to move the drive shaft 520 back inwardly towards the microneedling device during its reciprocating motion. Also, this alternative embodiment includes a single absorbing member 550 that provides a liquid barrier in accordance with the disclosed principles. Accordingly, the absorbing member 550 may be comprised of an absorbing material such as cotton to prevent patient blood and/or any liquid mixture being injected in the patient's skin from passing from the needle unit 515 through the base portion 505, and back into the main body of the microneedling device holding the needle cartridge 500. Thus, as before, the absorbing member 550 may be sized so that its external diameter contacts the interior surface of the base first portion 505a, and its internal diameter contacts the drive shaft 520. Moreover, the absorbing member 550 may be located so that it rests against one of the support members 535a, helping to keep it in position.

In addition, this embodiment of the disposable needle cartridge 500 also includes a seal member 560 attached to the outer surfaces of the bearing members 530a, 530b. As before, a distal end of the seal member 560 is sealed to the second bearing member 530b, which in turn is sealed against (by being coupled to or simply formed with) the first support member 535a, which in turn is sealed against (again, by being coupled to or simply formed with) the inner surface of the first base portion 505a. Thus, at this end of the seal member 560, backflowing liquid(s) would likely only pass through the area(s) between the drive shaft 520 and the aperture of the first support member 535*a*, which is sealed by the distal end of the seal member 560. Also, a proximal end of the seal member 560 is sealed to the first bearing member 530*a*, which in turn is sealed against the drive shaft 520. Thus, at this end of the seal member 560, backflowing liquid(s) would likely only pass over the first bearing member 530*a*, which is sealed by the proximal end of the seal member 560. Accordingly, the seal member 560 is provided at the base of the needle cartridge 500 as a further fluid/liquid barrier, in addition to the absorbing barrier provided by absorbing member 550, to further help prevent the backflow of blood discharged from the skin of a patient, as well as any injection liquid mixture, that may flow from the needle unit 515 through the base portion 505 and back to the main body of the microneedling device during a microneedling transdermal procedure.

The material comprising the seal member 560 may be any advantageous material that may provide an airtight or hermetic seal. For example, the seal member 560 may be made from one or more natural rubber material(s), such as latex, isoprene, polyisoprene and other natural elastomers, as well as one or more synthetic rubbers materials, such as styrene-butadiene rubbers (SBR) and other petroleum-derived synthetic elastomers. Of course, no limitation to the materials used for the seal member 560, or combinations thereof, is intended or should be implied. Accordingly, although not required, such a seal may be combined with the unique absorbing barrier of the disclosed principles to provide a combined protection structure against backflowing liquids from the needle unit 515 to the main body of the microneedling device on which the disposable needle cartridge 500 is mounted.

Also in this embodiment, the second support member 535*b* is configured to receive a portion of the attachment member 520*a* therethrough as the drive shaft 520 moves inwardly and outwardly during use. Additionally, as in the illustrated embodiment, the external shape of the attachment member 520*a* may again be formed with a non-circular shape. Likewise, the corresponding aperture 540, which may be seen looking briefly at FIG. 5A, of the second support member 535*b* may be of the same non-circular shape. Thus, as the aperture 540 of the second support member 535*b* receives the attachment member 520*a* therethrough during reciprocating movement of the drive shaft 520, the corresponding non-circular shapes of these components assist in preventing the drive shaft 520 from rotating about the longitudinal axis of the cartridge 500. Although the non-circular shape of the aperture 540, as well as the corresponding external shape of the portion of the attachment end 520*b* received therein, are illustrated as rectangular, it should be understood that any non-circular shape may be employed within the broad scope of the disclosed principles. Moreover, turning briefly to FIG. 5B, the first support member 535*a* and the absorbing member 550 may have circular apertures 540*a* therethrough, which would correspond to the cross-sectional shape of the drive shaft 520. In other embodiments, these components could additionally, or alternatively, have the non-circular cross-sectional/aperture shapes to assist in prevent rotation of the needle unit 515 during use of the cartridge 500. In yet other embodiments, all of the applicable components simply have corresponding circular shapes.

The embodiment of the needling cartridge 500 illustrated in FIG. 5 also differs from prior embodiments in that the depth adjustment sleeve 510 is configured to be received within the second base portion 505*b*, rather than over its exterior surface. As such, threads 505*c* are formed on the exterior surface of the proximal end of the depth adjustment sleeve 510, as well as on the interior surface of the distal end of the second base portion 505*b*. As with other embodiments, the threaded attachment of the depth adjustment sleeve 510 to the base portion 505*b* allows a user to precisely adjust the maximum distance the needles 515*a* of the needle unit 515 will longitudinally extend beyond the distal end 510*a* of the depth adjustment sleeve 510. A graduation scale (not illustrated) may thus be included on the external surface of the depth adjustment sleeve 510 such that the distal end of the second base portion 505*b* aligns with graduations on the exterior of the depth adjusting sleeve 510 indicating to a user the specific maximum distance the needles 515*a* will extend beyond the distal end 510*a* of the sleeve 510 during use of the injection device to which the cartridge 500 is attached. Also as before, the means by which the depth adjustment sleeve 510 is movably coupled to the base portion 505*b* may be different than the illustrated threaded attachment means, while still falling within the broad scope of the present disclosure.

Figure 6A:
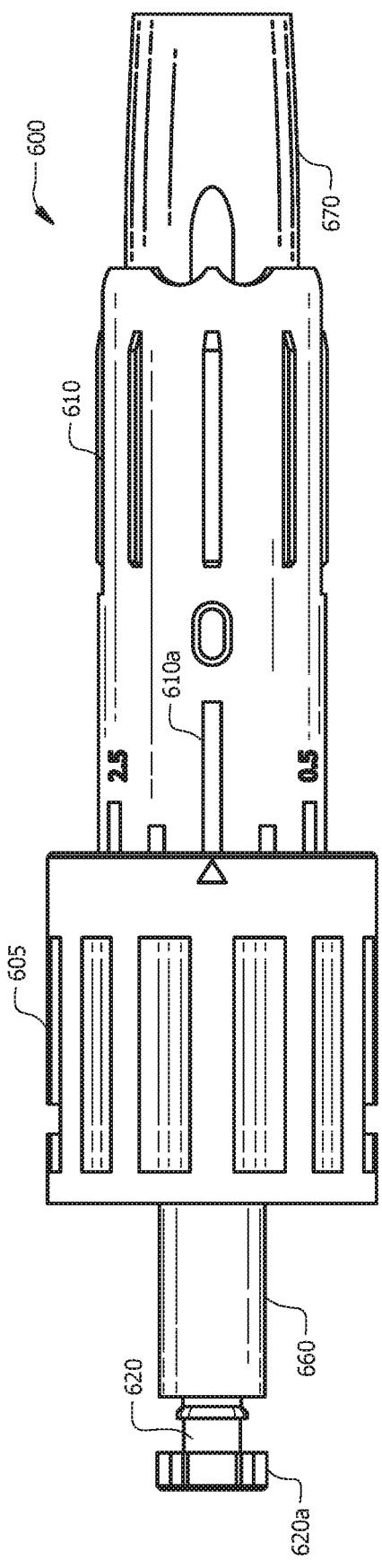
FIG. 6A illustrates a side view of yet another embodiment of a disposable needle cartridge constructed in accordance with the disclosed principles.
Figure 6B:
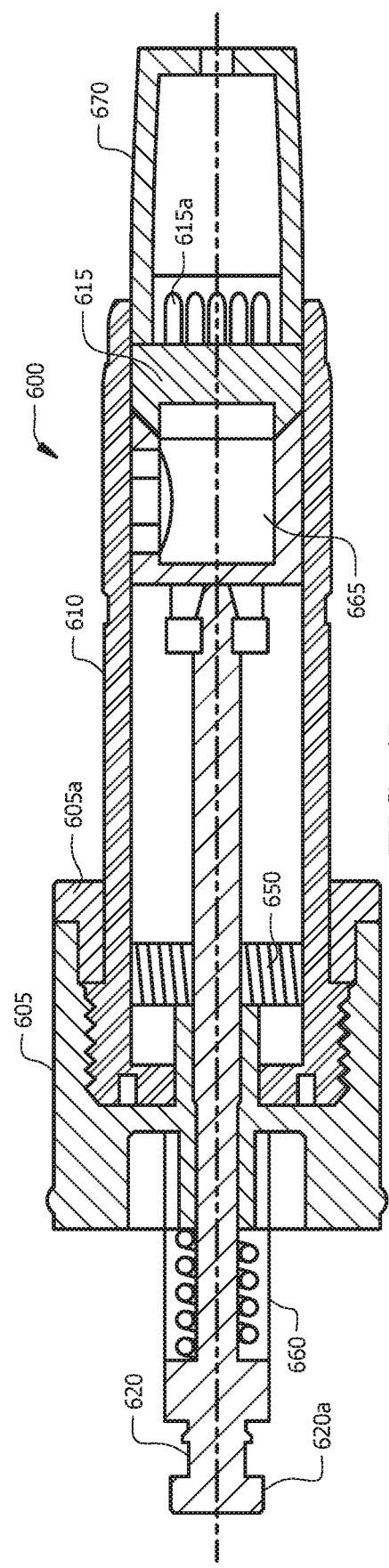
FIG. 6B illustrates a cross-sectional side view of the embodiment of a disposable needle cartridge illustrated in FIG. 6A.
Figure 6C:
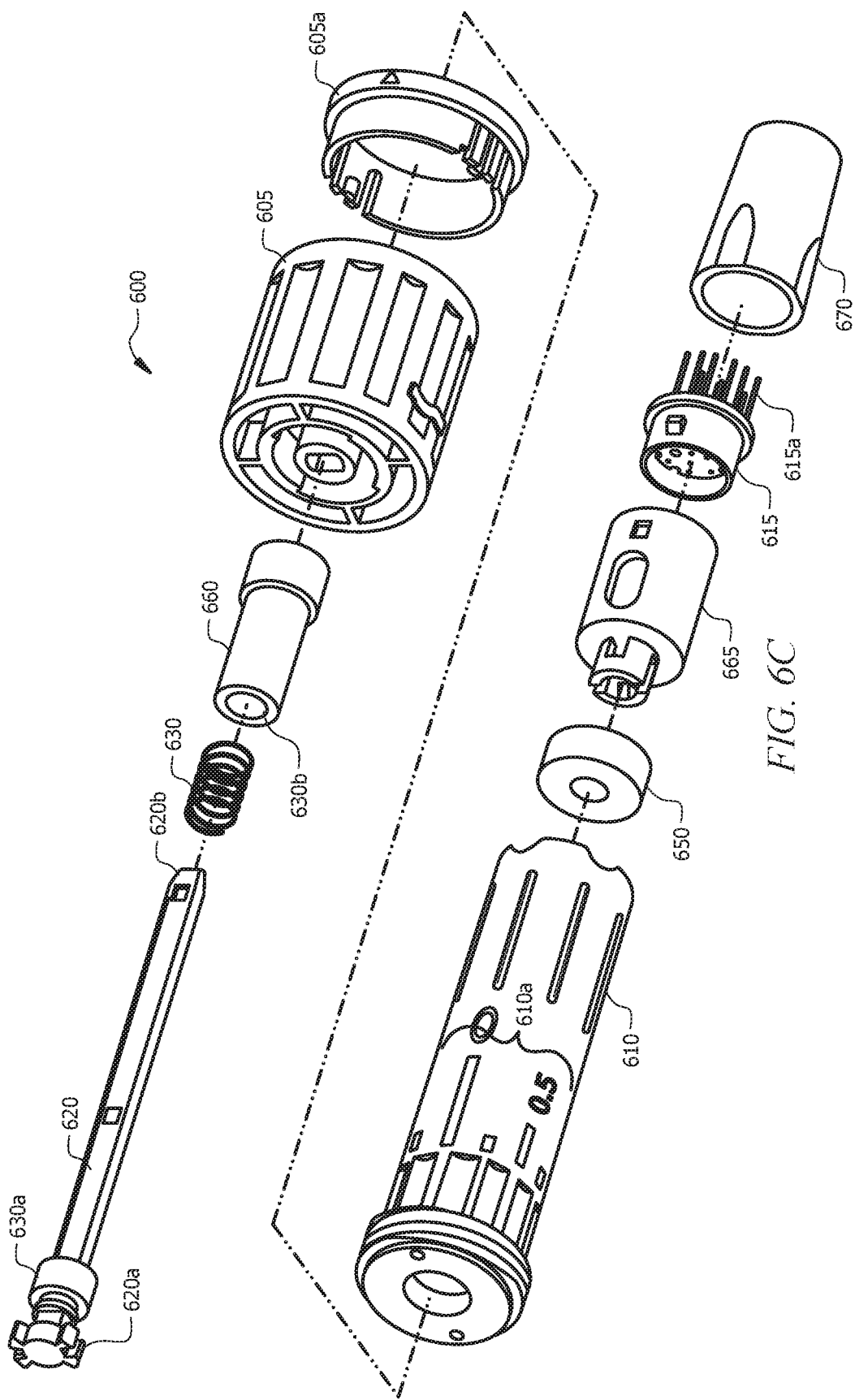
FIG. 6C illustrates an exploded view of the embodiment of a disposable needle cartridge illustrated in FIG. 6A and FIG. 6B.

Looking now collectively at FIG. 6A and FIG. 6B, illustrated are normal and cross-sectional side views, respectively, of yet another embodiment of a disposable needle cartridge 600 constructed in accordance with the disclosed principles. This embodiment of the needle cartridge 600 again includes a base portion 610, as well as a depth adjustment sleeve 605 and a needle unit 615. One end of the base portion 610 is moveably connected within the adjustment sleeve 605, for example, via a threaded connection. Also in this embodiment, the adjustment sleeve 605 cooperates with a retainer ring 605*a* to keep the base portion 610 in position, as well as to prevent the base portion 610 from extending too far. FIG. 6C illustrates an exploded view of this embodiment of the disposable needle cartridge 600. In this exploded view, the details of each of the individual components comprising the needle cartridge 600 may be seen, as well as one of the way they may be assembled into the finished cartridge 600.

As in other embodiments, this embodiment again includes a drive shaft 620 passing through the base portion 610 and adjustment sleeve 605, and attached to the base of the needle unit 615 using an attachment member attached to the attachment end of the drive shaft 620. The opposing, proximal end of the drive shaft 620 (proximal once again with respect to the microneedling device on which the cartridge 600 is mounted) again includes a cam member 620*b* for use in translating the rotation of a drive motor in the microneedling device (not illustrated) into longitudinal reciprocating motion of the drive shaft 620, as discussed in detail above.

This embodiment of the disposable needle cartridge 600 also again includes a coil spring 630 for pushing the drive shaft 620 back towards the main body of a microneedling device to which the needle cartridge 600 is attached to assist with the reciprocating motion of the drive shaft 620. The coil spring 630 again sits between first and second bearing surfaces 630*a*, 630*b* that cause the coil spring 630 to compress when the drive shaft 620 is moving outwardly, as well as provide the surfaces the compressed spring 630 pushes against to move the drive shaft 620 back inwardly towards the microneedling device during its reciprocating motion. Also, this embodiment includes a single absorbing member 650 that provides a liquid barrier in accordance with the disclosed principles. Accordingly, the absorbing member 650 may be comprised of an absorbing material such as cotton to prevent patient blood and/or any liquid mixture being injected in the patient's skin from passing from the needle unit 615 through the base portion 610, and back into the main body of the microneedling device holding the needle cartridge 600. Thus, as before, the absorbing member 650 may be sized so that its external diameter contacts the interior surface of the base portion 610, and its internal diameter contacts the drive shaft 620.

A liquid reservoir 665, which receives the needle unit 615 therein, may again be employed in some embodiments. As discussed above, such a reservoir 665 is used to hold the liquid(s) being injected into a patients skin during use of a liquid injection microneedling device holding the cartridge 600, and which may be dispensed into the reservoir 665 through a liquid dispensing aperture. Also in this embodiment as with others, a protective cap 670 may be provide to not only cover the needles 615a, but also to provide a seal for liquids that may be present in the reservoir 665.

In addition, this embodiment of the disposable needle cartridge 600 also includes a seal member 660 attached to the outer surfaces of the bearing members 630a, 630b. As before, a distal end of the seal member 660 is sealed to the second bearing member 630b, which in turn is sealed against (by being coupled to or simply formed with) a support member of the adjustment sleeve. Thus, at this end of the seal member 660, backflowing liquid(s) would likely only pass through the area(s) between the drive shaft 620 and the aperture of the support member, which is sealed by the distal end of the seal member 660. That this support member is part of the internal construction of the adjustment sleeve 605, rather than the base portion 610, is another unique feature of this embodiment. Also, a proximal end of the seal member 660 is sealed to the first bearing member 630a, which in turn is sealed against the drive shaft 620. Thus, at this end of the seal member 660, backflowing liquid(s) would likely only pass over the first bearing member 630a, which is sealed by the proximal end of the seal member 660. Accordingly, the seal member 660 is provided at the base of the needle cartridge 600 as a further fluid/liquid barrier, in addition to the absorbing barrier provided by absorbing member 650, to further help prevent the backflow of blood discharged from the skin of a patient, as well as any injection liquid mixture, that may flow from the needle unit 615 through the base portion 610 and back to the main body of the microneedling device during a microneedling transdermal procedure.

The material comprising the seal member 660 may again be any advantageous material that may provide an airtight or hermetic seal. For example, the seal member 660 may be made from one or more natural rubber material(s), such as latex, isoprene, polyisoprene and other natural elastomers, as well as one or more synthetic rubbers materials, such as styrene-butadiene rubbers (SBR) and other petroleum-derived synthetic elastomers. Of course, no limitation to the materials used for the seal member 660, or combinations thereof, is intended or should be implied. Accordingly, although not required, such a seal may be combined with the unique absorbing barrier of the disclosed principles to provide a combined protection structure against backflowing liquids from the needle unit 615 to the main body of the microneedling device on which the disposable needle cartridge 600 is mounted.

This embodiment of the needling cartridge 600 also differs from prior embodiments in that the depth adjustment sleeve 605 is configured to receive the proximal end of the base portion 610. As such, threads are formed on the exterior surface of the proximal end of the base portion 610, as well as on the interior surface of the distal end of the adjustment sleeve 605. As with other embodiments, the threaded attachment of the base portion 610 to the adjustment sleeve 605 allows a user to precisely adjust the maximum distance the needles 615a of the needle unit 615 will longitudinally extend beyond the distal end of the base portion 610. A graduation scale 610a may thus be included on the external surface of the base portion 610 such that the distal end of the adjustment sleeve 605 (where the retainer ring 605a is located) aligns with graduations on the exterior of the base portion 610 indicating to a user the specific maximum distance the needles 615a will extend beyond the distal end of the base portion 610 during use of the injection device to which the cartridge 600 is attached. Also as before, the means by which the depth adjustment sleeve 605 is movably coupled to the base portion 610 may be different than the illustrated threaded attachment means, while still falling within the broad scope of the present disclosure.

Turning now to FIG. 7A and FIG. 7B, illustrated is another embodiment of a disposable needle cartridge 700 constructed in accordance with the disclosed principles. This embodiment of the cartridge 700 includes the ability to emit radio frequency (RF) energy through the needles of the cartridge during their use in a microneedling procedure. FIG. 7A illustrates an exploded view of an exemplar embodiment of a disposable RF needle cartridge 700, while FIG. 7B illustrates the RF needle cartridge 700 fully assembled.

This RF embodiment of the needle cartridge 700 includes a housing 705, which is used to receive and hold an RF needle capsule 710. The RF needle capsule 710 is received within a distal end of the housing 705, and a safety cap 770 may be provided over the received RF needle capsule 710 to safely cover the needles (not illustrated) protruding from the RF needle capsule 710. The RF cartridge 700 also includes base 715 on which the housing 705 is mounted. The base 715 is configured to receive a drive shaft 720, which may be similar to drive shafts discussed above. The drive shaft 720 is configured to pass through the base 715, and in the illustrated embodiment, the drive shaft 720 has a non-circular cross section which corresponds to a matching aperture through the base 715. As in other embodiments, the drive shaft 720 may include a cam member 720a on its proximal end for use in translating the rotation of a drive motor in the microneedling device (not illustrated) on which the RF needle cartridge 700 is attached into longitudinal reciprocating motion of the drive shaft 720, as discussed above. The non-circular drive shaft 720 and the corresponding aperture in the base 715 cooperate to prevent the drive shaft 720 from rotating while it reciprocates within the base 715. Although the non-circular shape of the aperture in the base 715, as well as the corresponding external shape of the drive shaft 720 received therein, are illustrated as rectangular, it should be understood that any non-circular shape may be employed within the broad scope of the disclosed principles. A distal end of the drive shaft 720 is also configured to attach to a mount 710a on the proximal end of RF needle capsule 710, and thereby translates the longitudinal reciprocating motion of the drive shaft 720 into longitudinal reciprocation of the RF needle capsule 710 during use of the device. A seal 760, such as the seals discussed above, may again be provided over the proximal end of the drive shaft 720, which includes a coil spring (not illustrated) to assist in the shaft's reciprocating motion.

The base 715 of this embodiment of the disposable needle cartridge 700 may also be formed of at least two pieces, as illustrated, which are moveable with respect to one another. The connection of such movable pieces may permit twisting the pieces with respect to one another, which in turn can provide depth adjustment for the needle capsule. In such embodiments, one such component of the base 715 may include graduations 715a, with the other of the components having a chevron or other marker aligning with the graduations 715a. Thus, as the two components of the base 715 are twisted with respect to one another, the needle capsule 710 may be longitudinally moved within the housing 705 an amount indicated by the graduations 715a. This longitudinal movement of the RF needle capsule 710 within the housing 705 adjusts the amount the needles at the distal end of the needle capsule 710 extend beyond the distal end of the housing 705 during use of the RF cartridge 700 during a microneedling procedure. Although such a twisting configuration for adjusting the needle depth of the capsule 710 is illustrated, it should be noted that other configurations for adjusting the needle depth beyond the distal end of the housing 705 may also be employed, or no adjustment may be included at all.

Also, this RF embodiment of a disposable cartridge 700 again includes a single absorbing member 750 that provides a liquid barrier in accordance with the disclosed principles shown in other non-RF energy embodiments discussed in detail above. As before, the absorbing member 750 may be comprised of an absorbing material such as cotton to prevent patient blood and/or liquid mixture being injected in the patient's skin from passing from the RF needle capsule 710 through the housing 705, and back into the base 715 and thereby to the main body of the microneedling device holding the RF needle cartridge 700. Thus, the absorbing member 750 may be sized so that its external diameter contacts the interior surface of the housing 705 holding the RF needle capsule 710, and its internal diameter contacts the drive shaft 720 and the feature on the proximal end of the needle capsule 710 configured to affix the distal end of the drive shaft 720. Moreover, the absorbing member 750 may be located against the proximal end wall of the housing 705 so that it stays in place during reciprocating movement of the RF needle capsule 710.

Additionally, in some embodiments, the internal diameter of the absorbing member 750 may be non-circular to match the cross section of the drive shaft 720, and thereby provide an absorbing barrier against the reciprocating drive shaft 720. In other embodiments, the absorbing barrier 750 may have an internal diameter configured to receive the drive shaft mount 710a formed on the proximal end of the RF needle capsule 710. In yet other embodiments, the absorbing barrier 750 may be configured so that its internal diameter is configured to contact the external diameter of the drive shaft 720 on one side, and configured to contact the drive shaft mount 710a on the opposing side. Still further, two absorbing barriers 750 may be employed, one having an internal diameter configured to contact the external diameter of the drive shaft 720, and the other one configured to contact the drive shaft mount 710a, where the two absorbing barriers may be positioned side by side. However, it should be noted that RF energy needle cartridges in accordance with the disclosed principles can also be constructed without any such absorbing barrier(s), and such embodiments would still maintain the advantages of emitting RF energy during microneedling procedures as disclosed herein.

Figure 8A:
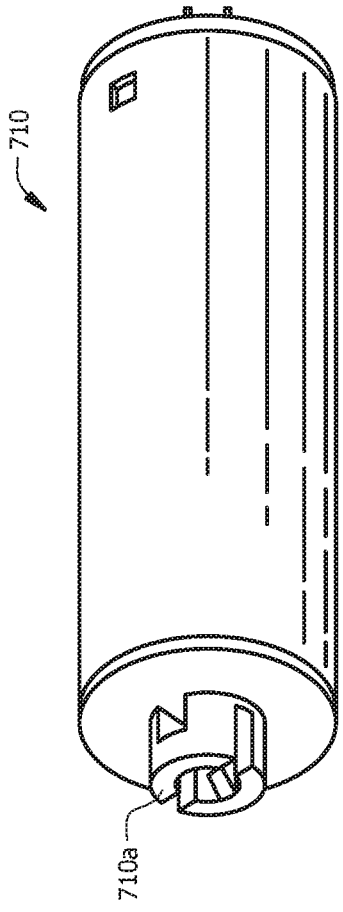
FIG. 8A illustrates a close up view of one embodiment of an RF needle capsule in accordance with the disclosed principles.
Figure 8B:
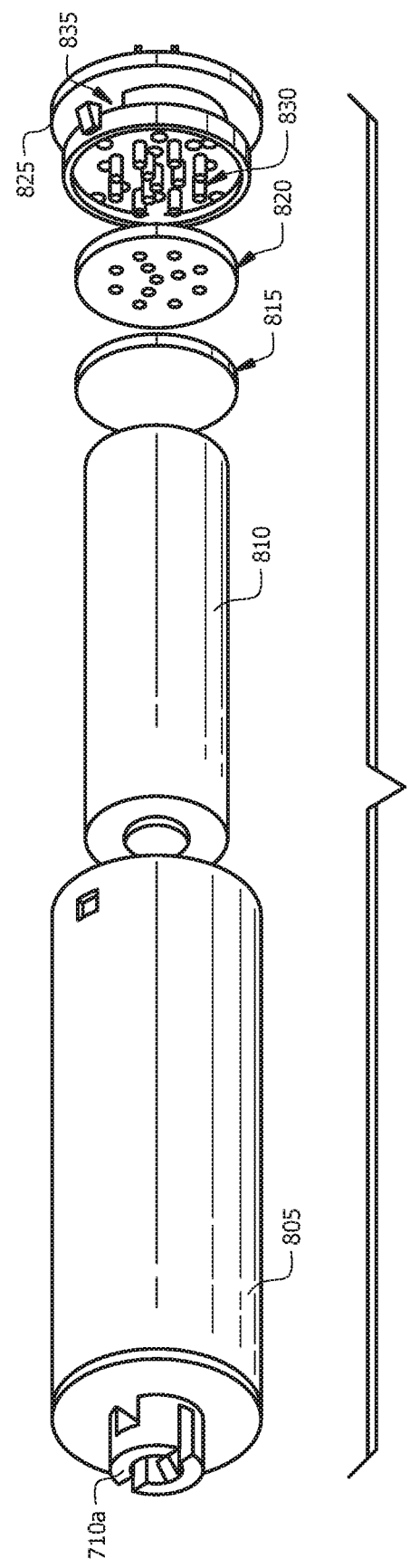
FIG. 8B illustrates an exploded view of the embodiment of an RF needle capsule illustrated in FIG. 8A.

Looking now at FIG. 8A and FIG. 8B, illustrated is a close up view of one embodiment of an RF needle capsule 710 in accordance with the disclosed principles. FIG. 8A illustrates an assembled RF needle capsule 710, while FIG. 8B illustrates an exploded view of the RF needle capsule 710 showing the components therein.

Among the components within the RF needle capsule 701 is a battery 810. The size of the battery 810 may be selected to slip fit within the capsule housing 805, which in exemplary embodiments may be size 27A. Of course, other models and sizes of batteries may be employed as the size of the needle capsule 710 is altered for various microneedling applications. Contacting a distal end of the battery 810 is an oscillator printed circuit board (PCB) 815. The oscillator PCB 815 would comprise an oscillator circuit configured to generate the RF energy to be applied with the RF needle capsule 710 during a microneedling application. The use of low energy RF signals during a microneedling procedure, for example, about 62 millijoules of energy, has been shown to advance the healing process of the human skin without ablating tissue or otherwise damaging the skin being treated. Thus, the oscillator PCB 815 can be configured to generate such low energy when powered by the battery 810 and when using the impedance of the skin when the needles 830 of the capsule 710 are contacting the person. Additionally, the oscillator circuit can also be configured to be adjustable during use of the microneedling device. This adjustment can thus raise or lower the RF energy generated and applied to the skin during the microneedling procedure.

To transfer the RF energy generated by the oscillator PCB 815 to the needles of the capsule 710, a needle contact PCB 820 may also be included. The needle contact PCB 820 is configured to receive the RF energy from the oscillator PCB 815, and distribute that energy from the needle contact PCB 820 to the needles 830 via contact areas or pads on the needle contact PCB 820. In an exemplary embodiment, the needles 830 pass through the needle contact PCB 820, with the apertures in the needle contact PCB 820 providing the transfer of RF energy to the needles 830, while in other embodiments the proximal ends of the needles 830 simply contact pads on the needle contact PCB 820. The needle unit 825 is included with the needle capsule 710 to hold the needles 830. The needle unit 825 may be configured to connect to the capsule housing 805 via snap fit, threaded, adhesive or any other type of connection. Also, the needle unit 825 may include a liquid reservoir 835. As discussed above, the reservoir 835 is configured to hold the liquid(s) being injected into a patients skin during use of a liquid injection microneedling device holding the cartridge 700. During use on a patient's skin, such as for tattooing or collagen injections, the liquid(s) pass through the needle unit 825 and onto the needles 830 extending form the distal end of the capsule 710.

Referring now to FIG. 9A and FIG. 9B, illustrated are side views of one embodiment of the RF needle capsule 710 in accordance with the disclosed principles illustrated in FIGS. 8A and 8B. FIG. 9A illustrates a side view of the RF needle capsule 710 in an assembled state, while FIG. 9B illustrates a side cross-sectional view of the assembled RF needle capsule 710 taken along line 9A-9B.

The cross-sectional view of FIG. 9B illustrates the location of each of the components of this embodiment of the RF needle capsule 710 when the capsule 710 is ready for joining to a microneedling pen or similar device (not illustrated) for use in a microneedling application. FIG. 9A reveals the battery 810 located within and towards the proximal end of the capsule housing 805 (as explained above, proximal with respect to the microneedling device onto which the RF needle capsule 710 is attached for use). With this positioning of the battery 810, an electrical contact is provided to electrically couple one end terminal of the battery 810 within the housing 805. At the distal end of the battery 810, the RF oscillator PCB 815 is positioned so as to electrically contact the opposing terminal end of the battery 810 when the RF needle capsule 710 is assembled. Located further distal of the battery is the needle contact PCB 820, which is positioned in electrical contact with the RF oscillator PCB 815 to receive the RF energy generated by the oscillator circuitry. At the far distal end of the RF needle capsule 710 is the needle unit 825, which includes the plurality of needles 830 use for the microneedling operation. These needles are placed in electric contact with the needle contact PCB 820 in order to receive the RF energy from the RF oscillator PCB 815. That low RF energy can then be transferred through the needles 830 to the skin of the patient receiving the microneedling operation. The liquid reservoir 835 is also illustrated within the needle unit 825, from which liquid(s) employed during the microneedling procedure can also be application to the patient's skin, such as through one or more apertures formed on the distal end or top of the needle unit 825, proximate to the needles 830.

It should be noted that while the cross-sectional view of FIG. 9B actually shows slight spacing between the various components of the RF needle capsule 710, such spaces are for clarity of illustration only in order to clearly show distinction between each component. However, in a manufactured embodiment of the RF needle capsule 710, physical, and thereby electrical contact, will be present between the proximal terminal end of the battery 810 and the capsule housing 805, as well as between the distal terminal end of the battery 810 and the RF oscillator PCB 815, between the RF oscillator PCB 815 and the needle contact PCB 820, and between the needle contact PCB 820 and the needles 830 of the needle unit 825. Additionally, in some embodiments, electrical contacts and/or circuitry may also be provided between any such components, or all of the components, of the capsule 710 as desired. Still further, an electrical switch may be provided between one or more of the components or circuitry to allow for manual On/Off switching of the RF oscillator circuitry 815 during use of the RF needle capsule 710 for a microneedling application.

Turning now to FIG. 10A and FIG. 10B, illustrated are side views of the disposable RF needle cartridge illustrated in FIG. 7A and FIG. 7B in an assembled state, and incorporating the RF needle capsule 710 illustrated in FIGS. 9A and 9B. FIG. 10A illustrates a side view of the disposable RF needle cartridge 700 in an assembled state, while FIG. 10B illustrates a cross-sectional side view of the RF needle cartridge 700 taken along line 10A-10B.

As discussed above, this embodiment of the disposable RF needle cartridge 700 includes a housing 705, used to receive and hold an RF needle capsule 710 therein, as well as a base 715 at a proximal end of the housing 705 and a safety cap 770 at the distal end of the housing to safely cover the needles 830 protruding from the RF needle capsule 710. Passing through the base 715 is the drive shaft 720, which also passes through the absorbing barrier 750 and connects to the mount 710a at the proximal end of the RF needle capsule 710. The drive shaft 720 includes the cam member 720a on its proximal end for use in translating the rotation of a drive motor in the microneedling device (not illustrated) on which the RF needle cartridge 700 is attached into longitudinal reciprocating motion of the drive shaft 720, as discussed above. The non-circular drive shaft 720 and the corresponding aperture in the base 715 cooperate to prevent the drive shaft 720 from rotating while it reciprocates within the base 715. By attaching the distal end of the drive shaft 720 to the mount 710a, and thereby translates the longitudinal reciprocating motion of the drive shaft 720 translates into longitudinal reciprocation of the RF needle capsule 710 during use of the device. A seal 760, such as the seals discussed above, is shown provided over the proximal end of the drive shaft 720, which includes a coil spring to assist in the shaft's reciprocating motion.

The base 715 of the disposable needle cartridge 700 may also be formed of two pieces, as illustrated, with the second piece 715b being an insert fitting within the base 715 and thus moveable with respect to one another. The connection of these two pieces in this embodiment permits twisting the pieces with respect to one another, which in turn can provide depth adjustment for the needle capsule 710 with respect to the distal end of the housing 705. Thus, as the two components of the base 715 are twisted with respect to one another, the needle capsule 710 may be longitudinally moved within the housing 705 an amount indicated by graduations (not illustrated). This longitudinal movement of the RF needle capsule 710 within the housing 705 adjusts the amount the needles at the distal end of the needle capsule 710 extend beyond the distal end of the housing 705 during use of the RF cartridge 700 during a microneedling procedure.

Also shown in the cross-sectional view of FIG. 10B is a single absorbing member 750 that provides a liquid barrier as discussed in detail above. The absorbing member 750 may be comprised of an absorbing material such as cotton to prevent patient blood and/or liquid mixture being injected in the patient's skin from passing from the RF needle capsule 710 through the housing 705, and back into the base 715 and thereby to the main body of the microneedling device holding the RF needle cartridge 700. Thus, the absorbing member 750 may be sized so that its external diameter contacts the interior surface of the housing 705 holding the RF needle capsule 710, and its internal diameter contacts the drive shaft 720. Moreover, the absorbing member 750 may be located against the proximal end wall of the housing 705, or it may be spaced slightly from that end of the housing 705 as illustrated. However, as noted above, RF energy needle cartridges in accordance with the disclosed principles can also be constructed without any such absorbing barrier(s), and such embodiments would still maintain the advantages of emitting RF energy during microneedling procedures as disclosed herein.

FIG. 10B also reveals the battery 810 located within and towards the proximal end of the capsule housing 805, as well as the RF oscillator PCB 815, the needle contact PCB 820, and the needle unit 825. The proximal end terminal of the battery 810 is in electrical contact with a contact at the proximal end of the housing 805, while the distal end of the battery 810 is in electrical contact with the RF oscillator PCB 815. In electrical contact with RF oscillator PCB 815 is the needle contact PCB 820, which as discussed above receives the RF energy generated by the oscillator circuitry. At the far distal end of the RF needle capsule 710 is the needle unit 825, which includes the plurality of needles 830 use for the microneedling operation. These needles 830 are placed in electric contact with the needle contact PCB 820 in order to receive the RF energy from the RF oscillator PCB 815. That RF energy is then transferred through the needles 830 to the skin of the patient receiving the microneedling operation. The liquid reservoir 835 is also illustrated within the needle unit 825, from which liquid(s) employed during the microneedling procedure can also be applied to the patient's skin.

Figure 11:
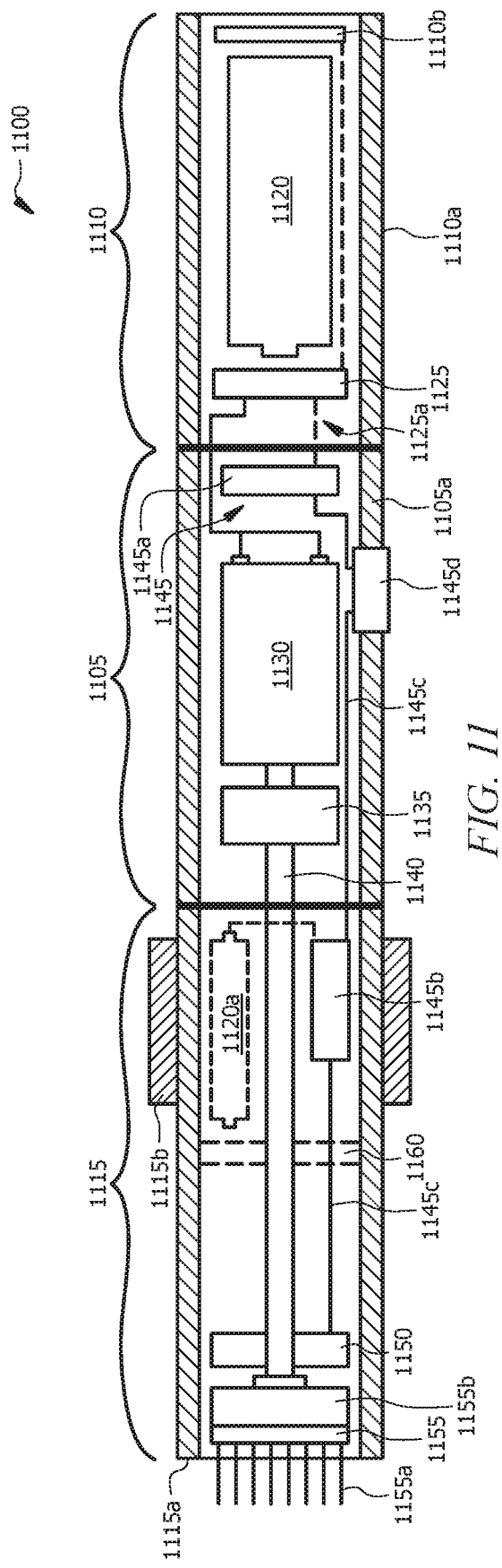
FIG. 11 illustrates a side cross-sectional view of another embodiment of an RF microneedling device designed and constructed in accordance with the disclosed principles.

Looking now at FIG. 11, illustrated is a side cross-sectional view of another embodiment of an RF microneedling device 1100 (which as discussed above may also be referred to as a microneedling pen) designed and constructed in accordance with the disclosed principles. Among the components comprising the RF needling device 1100 are a main body 1105, a battery capsule 1110, and an RF needling cartridge 1115. It should be noted that an exemplary RF microneedling device in accordance with the disclosed principles may include additional or fewer components, both within each compartment of the device 1100 or comprising portions of the device 1100 as a whole, yet still fall within the scope of the disclosed principles.

The illustrated embodiment of the battery capsule 1110 includes within the battery capsule housing 1110*a* a battery 1120 and battery management circuitry, which in this embodiment is a battery management PCB 1125. The size of the battery 1120 may again be selected to slip fit within the battery capsule housing 1110*a*, which in exemplary embodiments may be size 18650 or 18500. Of course, other models, sizes, voltages and/or capacities of batteries may be employed as the RF microneedling device 1100 is designed and constructed for various microneedling applications. At the proximal end of the battery 1120 is the battery management PCB 1125, where "proximal" is defined in this embodiment with respect to the positioning of the main body 1105 of the device 1100. The battery management PCB 1125 may be positioned so as to electrically contact the proximal terminal end of the battery 1120, or intermediate electrical circuitry and/or electrical contacts and other interconnections can also be employed. An electrical contact would also be included to contact the distal terminal of the battery 1120 and electrically couple it the battery management PCB 1125 as well.

The main body 1105 of the device 1100 includes a main body housing 1105*a* to which the battery capsule 1110 is configured to connect. In some embodiments, the battery capsule 1110 may be removably coupled to the main body housing 1105*a*, such as by a threaded or rotational interlocking connection. By being removable from the main body housing 1105*a*, the battery 1120 can be accessed for replacement, if needed. In other embodiments, the battery capsule housing 1110*a* may instead have its own removable portion for accessing the battery 1120 when needed, e.g., the distal end of the battery capsule housing 110*a* may be removed to gain access to the battery 1120. In yet other embodiments, the battery capsule 1110 as a whole may simply be designed to be entirely removed from the main body 1105 and replaced when required.

Within the main body housing 1105, the device 1100 includes an electric motor 1130, powered by the battery 1120 and used for driving the components in the needle cartridge 1115, as well as the remainder of the device 1100 in many embodiments. The needle cartridge 1115 of this embodiment of the microneedling device 1100 is removably connected to the main body 1105 of the device, and may again be manufactured as a disposable needle cartridge 1115. In addition, the needle cartridge 1115 may be provided in a two-piece construction, which in this embodiment is a needle cartridge housing 1115*a* mated with a depth adjustment sleeve 1115*b*. The connection of these two pieces in such embodiments may permit twisting the pieces with respect to one another, which in turn can provide depth adjustment for the device's needles with respect to the distal end of the needle cartridge 1115, as discussed in embodiment above. Thus, as these two components 1115*a*, 1115*b* of the needle cartridge 1115 are twisted with respect to one another, the needle unit (discussed further below) may be longitudinally moved within the cartridge 1115 an amount indicated by graduations (not illustrated). This longitudinal movement of the needle unit within the needle cartridge housing 1115*a* adjusts the amount the needles at the distal end of the needle cartridge 1115 extend beyond the distal end of the housing 1115*a* during use of the RF device 1100 during a microneedling procedure.

Also within the main body housing 1105 is a linkage mechanism 1135 for translating the turning of the electric motor 1130 to the movement of the needle unit in the needle cartridge 1115. In this embodiment, the linkage mechanism 1135 may be a cam system that translates the spinning of the electric motor 1130 within the main body 1105 into a reciprocating "in and out" motion used to drive the needle unit. More specifically, a drive shaft 1140, which may again have a non-circular cross-section if desired, extends from the needle cartridge 1115 and reaches within the main body housing 1105*a*. the linkage mechanism 1135 may then include on a proximal end of the drive shaft 1140 a shaft cam member configured to engage a corresponding motor cam member. As discussed above, the drive motor 1130 includes a rotor shaft that rotates during operation of the device 1100. The distal end of the rotor shaft is attached to the motor cam member such that it is rotated by the drive motor 1130. Within the linkage cam mechanism 1135, the rotation of the motor cam member is translated to the shaft cam member such that the shaft cam member is moved in and out, longitudinally with respect to the device 1100. As described above, the cam mechanism 1135 may comprise high and low surfaces within the motor cam member that contact the bottom surface of the shaft cam member as it rotates. During this rotation, as the protruding high surfaces come into contact with the shaft cam member, the drive shaft 1140 is pushed away from the motor cam member, and once the high surface no longer are in contact with the shaft cam member a coil spring (not illustrated) may be used to push the drive shaft 1140 back towards the main body 1105 such that the shaft cam member now contacts the low, non-protruding surfaces of the motor cam member. This mating of the two cam members continues to create the reciprocating motion of the drive shaft 1140. In other embodiments, the linkage mechanism 1135 or means between the drive shaft 1140 and the drive motor 1130 may have a different design. More specifically, a gear drive mechanism may be employed. Such embodiments can permit the drive shaft 1140 to be in non-parallel alignment with respect to the rotor shaft of the drive motor 1130. The microneedling device illustrated in FIG. 12 and discussed in detail below, provides such an embodiment.

Also included within the main body 1105 is RF generator circuitry 1145 for generating the RF energy that may be used during a microneedling procedure, as discussed above. In this embodiment, the RF generator circuitry 1145 includes an RF oscillator PCB 1145*a*. As described above, the oscillator PCB 1145*a* would comprise an oscillator circuit configured to generate the RF energy to be applied with the RF needle cartridge 1115 during an RF-based microneedling procedure. In exemplary embodiments, the RF generator circuitry 1145 is a high-voltage RF energy generator configured to create RF energy at 1 MHz @ 250-400 VAC (peak-to-peak). The oscillator PCB 1145*a* is powered by the battery 1120 in order to generate such low RF energy, and thus additional electrical contacts and/or circuitry 1125*a* between the battery management circuitry 1125 and the RF generator circuitry 1145 may also be provided within the device 1100. As before, the RF generator circuitry 1145 can also be configured to be adjustable during use of the microneedling device, which can thus raise or lower the RF energy generated and applied to the skin during the microneedling procedure. Also, although only a single oscillator PCB 1145*a* is illustrated in this embodiment of an RF microneedling device 1100, it is understood that a greater number of PCBs may be employed or even other types of electrical circuitry can be employed.

To transfer the RF energy generated by the oscillator PCB 1145a to the needle cartridge 1115, a transformer 1145b may be provided within the device 1100. In this embodiment, the transformer 1145b is positioned within the needle cartridge 1115, but it should be understood that it could be positioned within other portions of the device 1100, such as within the main body 1105 or the battery capsule 1110, as is also the case with the RF generation circuitry 1145. Moreover, multiple transformers may also be provided, as needed. Also included are electrical interconnections 1145c provided between the RF generation circuitry 1145, such as the oscillator PCB 1145a, and the transformer 1145b. Included in such interconnections 1145c may be electrical connections provided between the various components of the device 1100. In this illustrated embodiment, such electrical connections would be provided between the main body 1105 and the needle cartridge 1115, since the RF generating circuitry 1145 is in a different device component than the transformer(s) 1145b located in the needle cartridge 1115.

Also within the needle cartridge 1115 is a needle contact PCB 1150. The needle contact PCB 1150 is configured to receive the RF energy generated from the oscillator PCB 1145a and electrically transferred to the transformer 1145b via interconnections 1145c. Once energy is provided to the needle contact PCB 1150 from the transformer 1145b, the needle contact PCB 1150 distributes that RF energy to the needles of the needle cartridge 1115. More specifically, the needle cartridge 1115 again includes a needle unit 1155, which in turn has a plurality of needles 1155a extending therefrom for performing a microneedling procedure on a patient. The proximal end of the needle unit 1155 may be configured to connect to the distal end of the drive shaft 1140, and thereby reciprocally move along with the drive shaft 1140 during use of the device 1100. Also, the needle unit 1155 may again include a liquid reservoir 1155b configured to hold any liquid(s) being injected into a patient's skin during use of the microneedling device 1100. As the device is used in an RF-based microneedling procedure, the needle contact PCB 1150 distributes the RF energy from the needle contact PCB 1150 to the needles 1155a via contact areas or pads on the needle contact PCB 1150. As discussed above, the needles 1155a may be configured to pass through the needle contact PCB 1150, with the apertures in the needle contact PCB 1150 providing the transfer of RF energy to the needles 1155a, while in other embodiments the proximal ends of the needles 1155a simply contact pads on the needle contact PCB 1150. That low RF energy can then be transferred through the needles 1155a to the skin of the patient receiving the RF-based microneedling procedure.

Also, as noted previously, any illustrated spacing between the various components of the RF microneedling device 1100 are simply for clarity of illustration only in order to show distinction between each component. However, in a manufactured embodiment of the various components of the device 1100, physical and/or electrical contact is present between many such components. Additionally, in some embodiments, electrical contacts, interconnections, and/or circuitry may also be provided between any such components, or all of the components, of the device 1100. Additionally, the device 1100 may further include an ON/OFF switch 1145d among the RF generation circuitry 1145 so that a user of the device 1100 can choose whether to use RF energy with each particular application. Of course, such an activation switch may also be included among other circuitry or components of the device, such as within the transfer circuitry, as desired. Also, the switch 1145d or additional components of the RF generation circuitry 1145 may include one or more components for adjusting the amount or level of RF energy being generated. Including such RF energy adjusting component(s) in the device 1100 allows a user of the device 1100 to specifically adjust the amount of RF energy being generated, and thus being delivered at the needles 1155a, with each particular application. Still further, in embodiments where the power source is a rechargeable battery 1120, the device 1100 may also include circuitry 1110b for recharging the battery 1120. For example, such recharging circuitry 1110b may be included within the battery management circuitry 1125, or may be provided as separate circuitry, as illustrated, with electrical interconnections between the two. Moreover, such recharging circuitry 1110b may also be configured to provide wireless charging of the battery 1120.

Additionally, a second power source 1120a may be provided within the needling cartridge 1115, in addition to the power source 1120 included in the power source capsule 1110. In such embodiments, the second power source 1120a can work in electrical cooperation with the first power source (e.g., battery 1120) to power the device 1100 and the components therein. In one embodiment, one power source may be configured to independently power the RF generating circuitry 1145, while the other power source is configured to power the drive motor 1130 and other components. Alternatively, such a second power source may be used to boost the energy provided by the battery 1120 in the power source capsule 1110. For example, as discussed above, the RF energy being generated may be about 1 MHz @ 250-400 VAC (peak-to-peak); however, employing a battery 1120 that can power the drive motor 1130 of the device 1100 and also provide this high voltage could likely be too large for a handheld microneedling device 1100. Thus, the second power source 1120a can provide the high voltage needed to generate the RF energy, while allowing the battery 1120 drives other components of the device 1110, thus allowing it to be of less capacity than would be needed to power both the drive motor 1130 and the RF generating circuitry 1145. The second power source 1120a can be thus used to boost the power from the battery 1120 so that it is sufficient to power the RF generating circuitry 1145. In more specific embodiments, such second power source 1120a may be included in the needle cartridge 1115, as illustrated. The RF generating circuitry 1145 may also be moved into the needle cartridge 1115 in such embodiments; however, this is not necessarily required. Moreover, the second power source 1120a in such a needle cartridge 1115 may also be configured to be rechargeable, and thus distinct battery management circuitry for the second power source 1120a may also be provided in the needle cartridge 1115 or in another component of the device 1100.

In addition to the RF energy providing circuitry 1145 and associated components provided in this embodiment of a microneedling device 1100, this embodiment may again include an absorbing barrier 1160 that provides a liquid barrier during a microneedling procedure using the device 1100, as discussed in detail above. As illustrated, the drive shaft 1140, which passes through the needle cartridge 1115, also passes through an absorbing barrier 1160 located in the needle cartridge 1115. In the embodiment of FIG. 11, a single absorbing member 1160 comprises the barrier to liquid backflow back through the needle cartridge 1115 during its use on a patient. As in prior embodiments, the absorbing member 1160 may be comprised of an absorbing material such as cotton to prevent patient blood and/or liquid mixture (i.e., initially held in the reservoir 1155b of the needle unit 1155) being injected in the patient's skin from passing from the distal end of RF needle cartridge 1115 back towards the main body 1105 of the device 1100. In exemplary embodiments, the absorbing member 1160 may be sized so that its external diameter contacts the interior surface of the needle cartridge housing 1115a, and its internal diameter contacts the drive shaft 1140. Also, the absorbing member 1160 may be located against the proximal end wall of the needle cartridge housing 1115a, or it may be spaced slightly from that end of the housing 1115a. Moreover, more than one absorbing barrier 1160 may be provided in the needle cartridge 1115, as also discussed above. A seal (not illustrated), such as the seals discussed in above embodiments, may also be provided over the proximal end of the drive shaft 1140, which could then also include the coil spring (not illustrated) used to assist in the drive shaft's 1140 reciprocating motion during operation of the device 1100.

Figure 12:
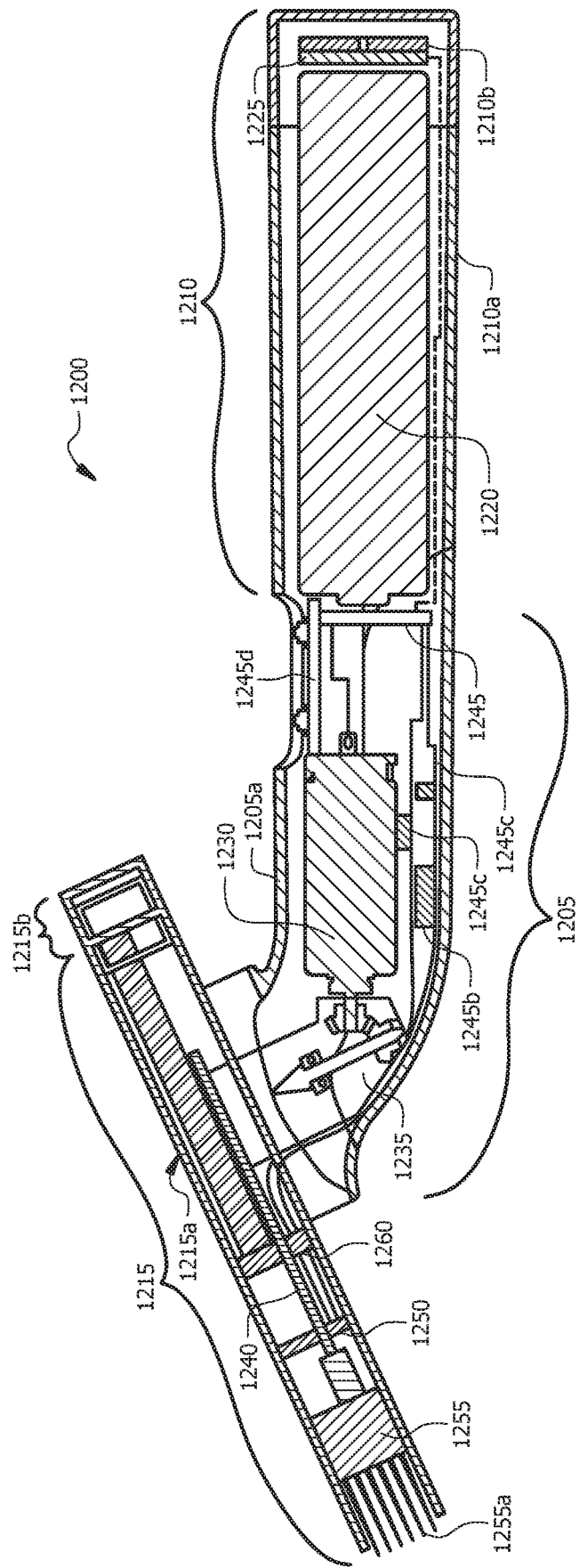
FIG. 12 illustrates a side cross-sectional view of yet another embodiment of an RF microneedling device designed and constructed in accordance with the disclosed principles.

Turning now to FIG. 12, illustrated is a side cross-sectional view of yet another embodiment of an RF microneedling device 1200 designed and constructed in accordance with the disclosed principles. This embodiment of an RF microneedling device 1200 again includes a main body 1205, a power source capsule 1210, and a needling cartridge 1215. However, this embodiment differs from the embodiment illustrated in FIG. 11 in that the needling cartridge 1215 is angularly offset with respect to the longitudinal axis of the main body 1205. As with other embodiments discussed herein, an exemplary RF microneedling device in accordance with this embodiment of the disclosed principles may include additional or fewer components, both within each compartment of the device 1200 or comprising portions of the device 1200 as a whole.

This embodiment of the battery capsule 1210 includes within the capsule housing 1210a a battery 1220 and battery management circuitry, which in this embodiment is again a battery management PCB 1225. The size of the battery 1220 may again be selected to slip fit within the battery capsule housing 1210a, such as battery size 18650 or 18500. Of course, other models, sizes, voltages and/or capacities of batteries may be employed as the RF microneedling device 1200 is designed and constructed for various microneedling applications. In this embodiment, the battery management PCB 1225 is located at the distal end of the battery 1220, where "distal" is again defined with respect to the positioning of the main body 1205. The battery management PCB 1225 may be positioned so as to electrically contact the distal terminal end of the battery 1220, or intermediate electrical contacts may be employed, as illustrated. Additional electrical interconnections 1225a may also be employed to electrically connect the power management PCB 1225 to proximal terminal of the battery 1220, as well as to control circuitry 1245 of the device 1200.

More specifically, the main body 1205 of the device 1200 includes a main body housing 1205a to which the battery capsule 1210 is configured to connect. As before, the battery capsule 1210 may be removably coupled to the main body housing 1205a, thus permitting the battery 1220 to be accessed for replacement, if needed. In other embodiments, the battery capsule housing 1210a may instead have a rear portion, which in this embodiment is proximate to the battery management PCB 1225, that is removable for accessing the battery 1220. Also within the main body housing 1205a is an electric motor 1230, which may be powered by the battery 1220 and used for driving the components in the needle cartridge 1215, as discussed below.

Also illustrated within the main body 1205 is the RF generator circuitry 1245 for generating the RF energy that may be used during a microneedling procedure, as discussed above. The RF generator circuitry 1245 may again include an RF oscillator PCB, which again may comprise an oscillator circuit configured to generate the RF energy to be applied with the RF needle cartridge 1215 during an RF-based microneedling procedure. The RF generator circuitry 1245 may be powered by the battery 1220, and thus additional electrical contacts and/or circuitry 1225a between the battery management circuitry 1225 and the RF generator circuitry 1245 may also be provided within the device 1200. To transfer the RF energy generated by the RF generator circuitry 1245 to the needle cartridge 1215, a transformer 1245b may be provided within the device 1200. In this embodiment, the transformer 1245b is positioned within the main body 1205, but it should be understood that it could be positioned within other portions of the device 1200, such as within the needle cartridge 1215 or the battery capsule 1210, as is also the case with the RF generation circuitry 1245. Moreover, multiple transformers may also be provided, as needed. Also included in the main body 1205 are electrical interconnections 1245c provided between the RF generation circuitry 1245 and the transformer 1245b, as well as to the needle cartridge 1215. As noted previously, any illustrated spacing between the various components of the RF microneedling device 1200 are simply for clarity of illustration only in order to show distinction between each component. However, in a manufactured embodiment of the various components of the device 1210, physical and/or electrical contact is present between many such components. Additionally, in some embodiments, electrical contacts, interconnections, and/or circuitry may also be provided between any such components, or all of the components, of the device 1200.

Additionally, the device 1200 may further include an ON/OFF switch 1245d connected to the RF generation circuitry 1245 so that a user of the device 1200 can choose whether to use RF energy with each particular application. The switch 1245d or additional components of the RF generation circuitry 1245 may also include one or more components for adjusting the amount or level of RF energy being generated. Including such RF energy adjusting component(s) in the device 1200 allows a user of the device 1200 to specifically adjust the amount of RF energy being generated, and thus being delivered at the needles 1255a, with each particular application. Still further, in embodiments where the power source is a rechargeable battery 1220, the device 1200 may also include circuitry 1210b for recharging the battery 1220. For example, such recharging circuitry 1210b may be included with the battery management circuitry 1225, as illustrated, with electrical interconnections between the two. Moreover, such recharging circuitry 1210b may also be configured to provide wireless charging of the battery 1220.

Also within the main body housing 1205 is a linkage mechanism 1235 for translating the turning of the electric motor 1230 to the movement of the needle unit 1255 in the needle cartridge 1215. In this embodiment, the linkage mechanism 1235 may be a geared system that translates the spinning of the electric motor 1230 within the main body 1205 into the reciprocating motion used to drive the needle unit 1255. More specifically, a drive shaft 1240, which may again have a non-circular cross-section if desired, extends through the needle cartridge 1215 and terminates at the needle unit 1255. The linkage mechanism 1235 may include a series of gears and complimentary mechanical components that mechanically interconnect with a proximal portion of the drive shaft 1240 to move it in this manner. For example, the rotor of the drive motor 1230 may include a bevel gear as its pinion gear, which in turn drives the geared mechanism within the linkage mechanism 1235. The linkage mechanism 1235 output would then connect to the drive shaft 1240, for example, in a worm gear connection, to create the reciprocating motion of the drive shaft 1240.

The needle cartridge 1215 of this embodiment of the microneedling device 1200 is also removably connected to the main body 1205 of the device, and may again be manufactured as a disposable needle cartridge 1215. In addition, the needle cartridge 1215 may be again include a depth adjustment mechanism 1215b, this time positioned at the rear of the needle cartridge 1215. As described above, the depth adjustment mechanism 1215b provides depth adjustment for the device's needles with respect to the distal end of the needle cartridge 1215. Thus, as the depth adjustment mechanism 1215b is turned, the needle unit 1255 is again longitudinally moved within the cartridge 1215 an amount indicated by graduations (not illustrated). This longitudinal movement of the needle unit 1255 within the needle cartridge housing 1215a adjusts the amount the needles 1255a at the distal end of the needle cartridge 1215 extend beyond the distal end of the housing 1215a during use of the RF device 1200 during a microneedling procedure. Also within the needle cartridge 1215 may be a needle contact PCB 1250. The needle contact PCB 1250 could again be configured to receive the RF energy generated from the RF generator circuitry 1245 and electrically transferred to the transformer 1245b via interconnections 1245c. Once energy is provided to the needle contact PCB 1250 from the transformer 1245b, the needle contact PCB 1250 again distributes that RF energy to the needles 1255a of the needle cartridge 1215. That RF energy can then be transferred through the needles 1255a to the skin of the patient receiving the RF-based microneedling procedure.

However, this embodiment of the needle cartridge 1215 is unique as it is configured to connect to the main body 1205 of the device in an angle configuration. More specifically, the longitudinal axis of the needle cartridge 1215, e.g., along which the drive shaft 1240 reciprocally translates during use of the device 1200, is positioned at an angle to, rather than being parallel with, the longitudinal axis of the main body 1205 and the power source capsule 1210. The linkage mechanism 1235 described above provides the mechanical interconnection between the rotor of the drive motor 1230 and the drive shaft 1240. In some embodiments, the needle cartridge housing 1215a may be integral with the main body, where the needle cartridge 1215 may then be received within that housing 1215a. In such embodiments, when the needle cartridge 1215 is replaced, it is simply slipped out of the integrally formed housing 1215a and a new, sterile cartridge 1215 is then placed within the housing 1215a. In alternative embodiments, the needle cartridge 1215 includes the housing 1215a, and the housing 1215a in turn includes a fastening mechanism that allows it to be removably connected to the main body 1205. Such a fastening mechanism may be snapping features that correspond to cooperating snapping features on the main body 1205, or the fastening mechanism may be a slide-lock design, with cooperating engaging features located on both the main body 1205 and the needle cartridge housing 1215a to permit the needle cartridge 1215 to be slid onto and locked into place on the main body 1205.

In such embodiments, the entire needle cartridge 1215 along with the housing 1215a are disconnected from the main body 1205 by unsnapping or sliding the housing 1215a off of the main body 1205. Of course, other mechanical connection between the main body 1205 and the needle cartridge housing 1215a may also be employed to provide the removable connection between these two components of the device 1200.

Additionally, as before a second power source (not illustrated) may be provided within the needling cartridge 1215, in addition to the power source 1220 included in the power source capsule 1210. As before, in such embodiments, the second power source 1220a can work in electrical cooperation with the first power source (e.g., battery 1220) to power the device 1200 and the components therein. For example, the second power source may be configured to independently power the RF generating circuitry 1245, while the battery 1220 is configured to power the drive motor 1230 and its related components. Alternatively, such a second power source may be used to boost the energy provided by the battery 1220 in the power source capsule 1210, as discussed above. Moreover, the second power source 1220a may also be configured to be rechargeable, and thus distinct battery management circuitry for the second power source 1220a may also be provided in the power source capsule 1210 or in another component of the device 1200.

As with other embodiments of the disclosed principles, this embodiment of a microneedling device 1200 may again include an absorbing barrier 1260 that provides a liquid barrier during a microneedling procedure using the device 1200, as discussed in detail above. As illustrated, the drive shaft 1240 within the needle cartridge 1215 also passes through such an absorbing barrier 1260, which provides the barrier to liquid backflow back through the needle cartridge 1215 and into the main body 1205 during use of the device 1200 on a patient. As in prior embodiments, the absorbing member 1260 may be comprised of an absorbing material such as cotton to prevent patient blood and/or liquid mixture being injected in the patient's skin from passing from the distal portion of RF needle cartridge 1215 back towards the main body 1205 of the device 1200. In exemplary embodiments, the absorbing member 1260 may again be sized so that its external diameter contacts the interior surface of the needle cartridge housing 1215a, and its internal diameter contacts the drive shaft 1240. Moreover, more than one absorbing barrier 1260 may be provided in the needle cartridge 1215, as also discussed above.

In the numerous embodiments of the inventive subject matter disclosed herein, such embodiments may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the claims reflect, inventive subject matter lies in less than all features of a single disclosed embodiment. Thus the following claims are hereby incorporated into the Detailed Description, with each claim standing on its own as a separate embodiment.

The description has made reference to several exemplary embodiments. It is understood, however, that the words that have been used are for description and illustration, rather than words of limitation. Changes may be made within the purview of the appended claims, as presently stated and as amended, without departing from the scope and spirit of the disclosure in all its aspects. Although this description makes reference to particular means, materials and embodiments, the disclosure is not intended to be limited to the particulars disclosed; rather, the disclosure extends to all functionally equivalent technologies, structures, methods and uses such as are within the scope of the appended claims.

What is claimed is:

1. A microneedling apparatus comprising:
   a main body comprising a main body housing, a needle cartridge housing, an electric motor in the main body housing, an angular drive housed in the main body housing, and a power source capsule; and
   a needle cartridge comprising a drive shaft, wherein the needle cartridge is removably coupled to and inserted within the needle cartridge housing; and
   wherein the angular drive is coupled between the electric motor and the drive shaft and is configured to convert rotary motion output from the electric motor into a linear motion of the drive shaft, the linear motion being a reciprocal motion along a longitudinal axis of the needle cartridge;
   wherein the drive shaft is only contained in the needle cartridge;
   wherein the longitudinal axis of the needle cartridge is inclined at an angle to, so as to not be parallel with, a longitudinal axis of the main body and the power source capsule; and
   wherein the needle cartridge is configured, during replacement of the needle cartridge with a new needle cartridge, to slide out of the needle cartridge housing, the new needle cartridge being configured to slide into the needle cartridge housing.

2. The microneedling apparatus of claim 1, wherein the needle cartridge comprises:
   a proximal end and a distal end, which is opposite the proximal end and is oriented for engagement with a patient's skin during operation of the microneedling apparatus; and
   a needle unit disposed at the distal end, the needle unit comprising a plurality of needles extending towards the distal end;
   wherein the drive shaft is coupled to the needle unit, the drive shaft being configured to be driven reciprocally along the longitudinal axis of the needle cartridge by the angular drive to thereby move the needle unit reciprocally along the longitudinal axis of the needle cartridge such that the plurality of needles of the needle unit extends beyond and retracts within the distal end of the needle cartridge.

3. The microneedling apparatus of claim 1, wherein the needle cartridge comprises:
   a proximal end and a distal end, which is opposite the proximal end and is oriented for engagement with a patient's skin during operation of the microneedling apparatus;
   a needle unit disposed at the distal end, the needle unit comprising at least one needle extending towards the distal end; and
   a needle extension adjuster disposed at the proximal end of the needle cartridge;
   wherein the drive shaft is coupled to the needle unit, the drive shaft being configured to be driven reciprocally along the longitudinal axis of the needle cartridge by the angular drive to thereby move the needle unit reciprocally along the longitudinal axis of the needle cartridge such that the at least one needle of the needle unit extends beyond and retracts within the distal end of the needle cartridge.

4. The microneedling apparatus of claim 3, wherein the at least one needle of the needle unit is a plurality of needles.

5. The microneedling apparatus of claim 3, wherein the needle cartridge is configured such that, when the needle extension adjuster is rotated, the needle unit moves within the needle cartridge along the longitudinal axis of the needle cartridge to adjust a needle extension distance that the at least one needle is allowed to extend beyond the distal end during operation of the microneedling apparatus.

6. The microneedling apparatus of claim 5, wherein the needle cartridge comprises graduations for indicating the needle extension distance to a user when the needle extension adjuster is rotated.

7. The microneedling apparatus of claim 1, wherein the electric motor further comprises a rotor coupled to the angular drive.

8. The microneedling apparatus of claim 1, wherein the needle cartridge comprises at least one needle coupled to a RF generation circuit.

9. The microneedling apparatus of claim 1, wherein the microneedling device is a handheld microneedling device.

10. The microneedling apparatus of claim 1, wherein the main body comprises a handle area for gripping by a user.

11. A microneedling apparatus comprising:
    a main body comprising a main body housing, an electric motor in the main body housing, an angular drive housed in the main body housing, and a power source capsule; and
    a needle cartridge housing; and
    a needle cartridge comprising a drive shaft and a needle unit comprising a plurality of needles, wherein the needle cartridge is removably coupled to and inserted within the needle cartridge housing;
    wherein the angular drive is coupled between the electric motor and the drive shaft and is configured to convert rotary motion output from the electric motor into a linear motion of the drive shaft, the linear motion being a reciprocal motion along a longitudinal axis of the needle cartridge;
    wherein the drive shaft is only contained in the needle cartridge; and
    wherein the longitudinal axis of the needle cartridge is inclined at an angle to, so as to not be parallel with, a longitudinal axis of the main body and the power source capsule.

12. The microneedling apparatus of claim 11, wherein the main body housing is integrally formed with the needle cartridge housing.

13. The microneedling apparatus of claim 11, wherein the needle cartridge further comprises:
- a proximal end and a distal end, which is opposite the proximal end and is oriented for engagement with a patient's skin during operation of the microneedling apparatus;
- wherein the needle unit is disposed at the distal end and the plurality of needles extends towards the distal end; and
- wherein the drive shaft is coupled to the needle unit, the drive shaft being configured to be driven reciprocally along the longitudinal axis of the needle cartridge by the angular drive to thereby move the needle unit reciprocally along the longitudinal axis of the needle cartridge such that the plurality of needles of the needle unit extends beyond and retracts within the distal end of the needle cartridge.

14. The microneedling apparatus of claim 13, wherein the needle cartridge comprises a needle extension adjuster, wherein the needle cartridge is configured such that, when the needle extension adjuster is rotated, the needle unit moves within the needle cartridge along the longitudinal axis of the needle cartridge to adjust a needle extension distance that the plurality of needles is allowed to extend beyond the distal end during operation of the microneedling apparatus.

15. The microneedling apparatus of claim 14, wherein the needle cartridge comprises graduations for indicating the needle extension distance to a user when the needle extension adjuster is rotated.

16. The microneedling apparatus of claim 11, wherein:
- the electric motor further comprises a rotor coupled to the angular drive; or
- the needle cartridge comprises at least one needle coupled to a RF generation circuit.

* * * * *